United States Patent [19]
Shen et al.

[11] Patent Number: 6,093,692
[45] Date of Patent: Jul. 25, 2000

[54] METHOD AND COMPOSITIONS FOR LIPIDIZATION OF HYDROPHILIC MOLECULES

[75] Inventors: Wei-Chiang Shen, San Marino; Jinghua Wang, South Pasadena, both of Calif.

[73] Assignee: The University of Southern California, Los Angeles, Calif.

[21] Appl. No.: 08/936,898

[22] Filed: Sep. 25, 1997

Related U.S. Application Data

[60] Provisional application No. 60/049,499, Jun. 13, 1997, and provisional application No. 60/077,177, Sep. 26, 1996.

[51] Int. Cl.[7] ................................................ A61K 38/28
[52] U.S. Cl. .................. 514/3; 514/2; 514/9; 514/19; 514/23; 530/300; 530/303; 530/307; 530/315; 530/317; 530/331; 530/333; 530/350
[58] Field of Search ................................ 514/2, 3, 9, 19, 514/23; 530/300, 303, 307, 315, 317, 331, 333, 350

[56] References Cited

U.S. PATENT DOCUMENTS

| 5,599,903 | 2/1997 | Kauvar et al. | 530/331 |
| 5,629,020 | 5/1997 | Leone-Bay et al. | 424/489 |
| 5,635,380 | 6/1997 | Naftilan et al. | 435/172.3 |
| 5,679,643 | 10/1997 | Kauvar et al. | 514/18 |
| 5,708,146 | 1/1998 | Willner et al. | 530/387.3 |
| 5,763,570 | 6/1998 | Kauvar et al. | 530/331 |

FOREIGN PATENT DOCUMENTS

| 0 482 766 | 4/1992 | European Pat. Off. |
| 63-246382 | 10/1988 | Japan . |
| WO 91/16067 | 10/1991 | WIPO . |
| WO 96/22773 | 8/1996 | WIPO . |

OTHER PUBLICATIONS

Artursson, P. and C. Magnusson, "Epithelial Transport of Drugs in Cell Culture. II: Effect of Extracellular Calcium Concentration on the Paracellular Transport of Drugs of Different Lipophilicities across Monolayers of Intestinal Epithelial (Caco–2) Cells," *J. Pharm. Sci.* 79(7): 595–600 (1990).

Broadwell, R. et al., "Transcytotic pathway for blood–borne protein through the blood–brain barrier," *Proc. Natl. Acad. Sci. USA* 85(2):632–636 (1988).

Brocklehurst, K. et al., "Preparation of Fully Active Papain From Dried Papaya Latex," *Biochem. J.* 133(1):573–584 (1973).

Chekhonin, V. et al., "Fatty acid acylated Fab–fragments of antibodies to neurospecific proteins as carriers for neuroleptic targeted delivery in brain," *FEBS Letters* 287(1,2):149–152 (1991).

Chu, Y. et al., "High–Potency Hybrid Compounds Related to Insulin and Amphioxus Insulin–like Peptide," *Biochem.* 33(44):13087–13092 (1994).

Conradi, R. et al., "The Influence of Peptide Structure on Transport Across Caco–2 Cells," *Pharm. Res.* 8(12):1453–1460 (1991).

Edwards, P., "Is Mucus A Selective Barrier To Macromolecules?" *British Med. Bulletin* 34(1):55–56 (1978).

(List continued on next page.)

*Primary Examiner*—Deborah Carr
*Attorney, Agent, or Firm*—Sterne, Kessler, Goldstein & Fox, P.L.L.C.

[57] ABSTRACT

Fatty acid derivatives of disulfide-containing compounds (for example, disulfide-containing peptides or proteins) comprising fatty acid-conjugated products with a disulfide linkage are employed for delivery of the compounds to mammalian cells. This modification markedly increases the absorption of the compounds by mammalian cells relative to the rate of absorption of the unconjugated compounds, as well as prolonging blood and tissue retention of the compounds. Moreover, the disulfide linkage in the conjugate is quite labile in vivo and thus facilitates intracellular or extracellular release of the intact compounds from the fatty acid moieties.

26 Claims, 13 Drawing Sheets

OTHER PUBLICATIONS

Ekrami, H., "Positively–Charged and Lipophilic Bowman–Birk Protease Inhibitor Conjugates: Synthesis and Characterization of the Pharmaceutical and Chemopreventive Properties," A Dissertation, UMI Dissertation Services, Ann Arbor, MI, Chapter 11, pp. 98–226 (after Jan. 25, 1995).

Ekrami, H. et al., "Water–soluble fatty acid derivatives as acylating agents for reversible lipidization of polypeptides," *FEBS Letters* 371(3):283–286 (Sep. 1995).

Eriksson, S. and B. Mannervik, "A method for the direct recording of an enzyme–catalyzed thiol–disulfide interchange using a mixed disulfide of glutathione and 3–carboxy–4–nitrobezenethiol," *Biochim. Biophys. Acta E* 212(3):518–520 (1970).

Eriksson, S. and B. Mannervik, "Direct recording of an enzyme–catalyzed thiol–disulfide interchange using a mixed disulfide of glutathione and 3–carboxy–4–nitrobezenethiol," *Chem. Abstracts* 73: 25, Abstract No. 127175y (1970).

Fix, J. et al., "Acylcarnitines: drug absorption–enhancing agents in the gastrointestinal tract," *Amer. J. Physiology* 251(3, Prt 1):G332–G340 (1986).

Friden, P. and L. Walus, "Transport Of Proteins Across The Blood–Brain Barrier Via The Transferrin Receptor," In: *Frontiers In Cerebral Vascular Biology, Transport and Its Regulation*, L. Drewes and A. Betz, eds. Plenum Press publ. New York pp. 129–136 (1993).

Gonzalez–Mariscal, L. et al., "Tight Junction Formation in Cultured Epithelial Cells (MDCK)," *J. Membrane Biol.* 86(2):113–125 (1985).

Gordon, G. et al., "Nasal absorption of insulin: Enhancement by hydrophobic bile salts," *Proc. Natl. Acad. Sci. USA* 82(21):7419–7423 (1985).

Hashimoto, M. et al., "Synthesis of Palmitoyl Derivatives of Insulin and Their Biological Activities," *Pharm. Res.* 6(2):171–176 (1989).

Huang, W. et al., "Lipophilic Multiple Antigen Peptide System For Peptide Immunogen And Synthetic Vaccine," *Mol. Immunol.* 31(15):1191–1199 (1994).

Hughes, R. et al., "Lipidic Peptides. III: Lipidic Amino Acid Oligomer Conjugates of Morphine," *J. Pharm. Sci.* 80(12):1103–1105 (1991).

Hughes, R. et al., "Lipidic Peptides. V: Penicillin and Cephalosporin Acid Conjugates with Increased Lipophilic Character," *J. Pharm. Sci.* 81(8):845–848 (1992).

Inagaki, M. et al., "Macromolecular permeability of the tight junction of the human nasal mucosa," *Rhinology* 23(3):213–221 (1985).

Kabanov, A. et al., "Lipid modification of proteins and their membrane transport," *Protein Engineering* 3(1):39–42 (1989).

Kajii, H. et al., "Fluorescence Study On The Interaction Of Salicylate With Rat Small Intestinal Epithelial Cells: Possible Mechanism For The Promoting Effects Of Salicylate On Drug Absorption In Vivo," *Life Science* 37(6):523–530 (1985).

Kidron, M. et al., "The Absorption Of Insulin From Various Regions Of The Rat Intestine," *Life Sci.* 31(25):2837–2841 (1982).

Landolph, J., "Chemical Transformation In C3H 10T½ C1 8 Mouse Embryo Fibroblasts: Historical Background, Assessment Of The Transformation Assay, And Evolution And Optimization Of The Transformation Assay Protocol," In: *Transformation Assay of Established Cell Lines: Mechanisms and Application*. T. Kakunaga and H. Yamasaki, eds. IARC Scientific Publications 67:185–203 (1985).

Lee, V., "Enzymatic barriers to peptide and protein absorption," *Crit. Rev. Ther. Drug Carrier Syst.* 5(2):69–97 (1988).

Lee, V. et al., "Mucosal penetration enhancers for facilitation of peptide and protein drug absorption," *Crit. Rev. Ther. Drug Carrier Syst.* 8(2):91–192 (1991).

Letsinger, R. et al., "Cholesteryl–conjugated oligonucleotides: Synthesis, properties, and activity as inhibitors of replication of human immunodeficieny virus in cell culture," *Proc. Natl. Acad. Sci.* 86(17):6553–6556 (1989).

Lowry, O. et al., "Protein Measurement With The Folin Phenol Reagent," *J. Biol. Chem.* 193:265–275 (1951).

Martins, M. et al., "Acylation of L–asparaginase with total retention of enzymatic activity," *Biochimie* 72(9):671–675 (1990).

McConahey, P. and F. Dixon, "Radioiodination of proteins by the use of the chloramine–T method," *Methods Enzymol.* 70(A):210–213 (1980).

Mostov, K. and N. Simister, "Transcytosis," *Cell* 43(2):389–390 (1985).

Muranishi, S. et al., "Lipophilic Peptides: Synthesis of Lauroyl Thyrotropin–Releasing Hormone and its Biological Activity," *Pharm. Res.* 8(5):649–652 (1991).

Reznikoff, C. et al., "Establishment and Characterization of a Cloned Line of C3H Mouse Embryo Cells Sensitive to Postconfluence Inhibition of Division," *Cancer Res.* 33(12):3231–3238 (1973).

Reznikoff, C. et al., "Quantitative and Qualitative Studies of Chemical Transformation of Cloned C3H Mouse Embryo Cells Sensitive to Postconfluence Inhibition of Cell Division," *Cancer Res.* 33(12):3239–3249 (1973).

Sett, R. et al., "Macrophage–Directed Delivery of Doxorubicin Conjugated to Neoglycoprotein Using Leishmaniasis as the Model Disease," *J. Infectious Dis.* 168(4):994–999 (1993).

Shen, W. C. and H. Ryser, "Poly(L–Lysine) has different membrane transport and drug–carrier properties when complexed with heparin," *Proc. Natl. Acad. Sci. USA* 78(12):7589–7593 (1981).

Shen, W. C. et al.,"Enhancement of polypeptide and protein absorption by macromolecular carriers via endocytosis and transcytosis," *Adv. Drug Delivery Rev.* 8(1):93–113 (1992).

Smith, P. et al., "Oral absorption of peptides and proteins," *Adv. Drug Delivery Rev.* 8(2,3):253–290 (1992).

Takaori, K. et al., "The Transport Of An Intact Oligopeptide Across Adult Mammalian Jejunum," *Biochem. Biophys. Res. Comm.* 137(2):682–687 (1986).

Taub, M. and W. C. Shen, "Polarity in the Transcytotic Processing of Apical and Basal Membrane–Bound Peroxidase–Polylysine Conjugates in MDCK Cells," *J. Cell Phys.* 150(2):283–290 (1992).

Toth, I., "A Novel Chemical Approach to Drug Delivery: Lipidic Amino Acid Conjugates," *J. Drug Targeting* 2(3):217–239 (1994).

Ubuka, T. et al., "Synthesis of disulfides related to glutathione and their detection in tissue," (*Ganryu Aminosan*) *Sulfur Amino Acids* 8(1):153–157 (1985).

Ubuka, T. et al., "Synthesis of disulfides related to glutathione and their detection in tissue," *Chem. Abstracts* 106:728, Abstract No. 156843v (1987).

Uchimi, I. et al., "Glutathione derivatives," *Chem. Abstracts* 73:11, Abstract No. 56440t (1970).

Uchimi, I. et al., "Glutathione derivatives," *Chem. Abstracts* 74:11, Abstract No. 54179m (1971).

Větvička, V. and L. Fornůsek, "Limitations Of Transmembrane Transport In Drug Delivery," *Crit. Rev. Ther. Drug Carrier Syst.* 5(3):141–170 (1988).

Vitetta, E., "Immunotoxins: New therapeutic reagents for autoimmunity, cancer, and AIDS," *J. Clin. Immunol.* 10(6 Suppl):15S–18S (1990).

Wan, J. et al., "Transcellular Processing of Disulfide–and Thioether–Linked Peroxidase–Polylysine Conjugates in Cultured MDCK Epithelial Cells," *J. Cell. Phys.* 145(1):9–15 (1990).

Wan, J. and W. C. Shen, "Brefeldin A And Monensin Enhance Transferrin Receptor–Mediated Protein Transport Across Epithelial Cells," *Pharm. Res.* 8(10)Suppl:S–4 (1991).

Wan, J. et al., "Brefeldin A Enhances Receptor–mediated Transcytosis of Transferrin in Filter–grown Madin–Darby Canine Kidney Cells," *J. Biol. Chem.* 267(19):13446–13450 (1992).

Yavelow, J. et al., "Bowman–Birk Soybean Protease Inhibitor as an Anticarcinogen," *Cancer Res.* 43(5)Suppl:2454s–2459s (1983).

Yodoya, E. et al., "Enhanced Permeability of Tetragastrin across the Rat Intestinal Membrane and Its Reduced Degradation by Acylation with Various Fatty Acids," *J. Pharm. Ex. Ther.* 271(3):1509–1513 (1994).

Yoshikawa, H. et al., "Potentiation of Enteral Absorption of Human Interferon Alpha and Selective Transfer into Lymphatics in Rats," *Pharm. Res.* 5:249–250 (1985).

STN Information Service: File Registry, RN 23130–02–1.

Patent Abstract of Japanese Publication No. 63246382, obtained from the European Patent Office.

Müller, C. et al., "Lipophilic disulfide prodrugs–syntheses and disulfide bond cleavage," *International J. Pharmaceutics* 57:41–47 (1989).

6,093,692

METHOD AND COMPOSITIONS FOR LIPIDIZATION OF HYDROPHILIC MOLECULES

This application claims the benefit of provisional applications 60/077,177, filed Sep. 26, 1996, and 60/049,499, filed Jun. 13, 1997.

FIELD OF THE INVENTION

The present invention relates generally to the fields of biology and medicine. More particularly, the present invention is directed to methods and compositions useful in increasing in mammals the absorption and retention of hydrophilic molecules, in particular peptides and proteins.

BACKGROUND OF THE INVENTION

Advances in biotechnology have made possible the production of large amounts of therapeutically active and pure proteins and peptides. Currently, the therapeutic effects of most of these agents can be achieved only when they are administered via invasive routes, such as by injection. Since most proteins have very short half lives, effective concentrations of these agents can be maintained only when administered by frequent injections.

Although the administration of proteins by injection is the most effective means of their delivery in vivo, patient tolerance of multiple injections is very poor. In addition, drug injection requires training and skill that may not always be transferable to patients. In cases where protein drugs have a life-saving role, the administration by injection can be accepted by the patients. However, in cases where protein drugs are just one of several possible therapies, injections of proteins and peptides are unlikely to be accepted by the patients. Therefore, alternative routes of protein and peptide delivery need to be developed.

Such alternative routes may include the buccal, nasal, oral, pulmonary, rectal and ocular routes. Without exception, these routes are less effective than the parenteral routes of administration, but are still far more attractive than the parenteral routes because they offer convenience and control to the patients. The oral route is particularly attractive because it is the most convenient and patient-compliant.

Mucosal barriers, which separate the inside of the body from the outside (e.g. GI, ocular, pulmonary, rectal and nasal mucosa), comprise a layer of tightly joined cell monolayers which strictly regulate the transport of molecules. Individual cells in barriers are joined by tight junctions which regulate entry into the intercellular space. Hence, the mucosa is at the first level a physical barrier, transport through which depends on either the transcellular or the paracellular pathways [Lee, V. H. L., *CRC. Critical Rev. Ther. Drug Delivery Sys.*, 5:69–97 (1988)].

Paracellular transport through water filled tight junctions is restricted to small molecules (MW <1 kDa) and is essentially a diffusion process driven by a concentration gradient across the mucosa [Lee, (1988), supra; Artursson, P., and Magnusson, C., *J. Pharm. Sci.*, 79:595–600 (1990)]. The tight junctions comprise less than 0.5% of the total surface area of the mucosa [Gonzalez-Mariscal, L. M. et al., *J. Membrane. Biol.*, 86:113–125 (1985); Vetvicka, V., and Lubor, F., *CRC Critical Rev. Ther. Drug Deliv. Sys.*, 5:141–170 (1988)]; therefore, they play only a minor role in the transport of protein drugs across the mucosa.

The transcellular transport of small drugs occurs efficiently provided the physiochemical properties of the drug are suited to transport across hydrophobic cell barriers. However, the transcellular transport of proteins and peptides is restricted to the process of transcytosis [Shen, W. C., et al., *Adv. Drug Delivery Rev.*, 8:93–113 (1992)]. Transcytosis is a complex process in which proteins and peptides are taken up into vesicles from one side of a cell, and are subsequently shuttled through the cell to the other side of the cell, where they are discharged from the endocytic vesicles [Mostov, K. E., and Semister, N. E., *Cell*, 43:389–390 (1985)]. The cell membrane of mucosal barriers is a hydrophobic lipid bilayer which has no affinity for hydrophilic, charged macromolecules like proteins and peptides. In addition, mucosal cells may secrete mucin which can act as a barrier to the transport of many macromolecules [Edwards, P., *British Med. Bull.*, 34:55–56 (1978)]. Therefore, unless specific transport mechanisms exist for protein and peptide, their inherent transport across mucosal barriers is almost negligible.

In addition to providing a tight physical barrier to the transport of proteins and peptides, mucosal barriers possess enzymes which can degrade proteins and peptides before, after, and during their passage across the mucosa. This barrier is referred to as the enzymatic barrier. The enzymatic barrier consists of endo- and exopeptidase enzymes which cleave proteins and peptides at their terminals or within their structure. Enzymatic activity of several mucosa have been studied and the results demonstrated that substantial protease activity exists in the homogenates of buccal, nasal, rectal and vaginal mucosa of albino rabbits and that these activities are comparable to those present in the ilium [Lee, et al., (1988), supra]. Therefore, regardless of the mucosa being considered, the enzymatic barrier present will feature strongly in the degradation of the protein and peptide molecules.

The N and the C termini of peptides are charged and the presence of charged side chains imparts highly hydrophilic characteristics on these macromolecules. In addition, the presence of charged side chains means that proteins and peptides have strong hydrogen bonding capacities; this H-bonding capacity has been demonstrated to play a major role in inhibiting the transport of even small peptides across cell membranes [Conradi, R. A., et al., *Pharm. Res.*, 8:1453–1460 (1991)]. Therefore, the size and the hydrophilic nature of proteins and peptides combine to severely restrict their transport across mucosal barriers.

One approach that has been used to alter the physical nature of the mucosal barriers is the use of penetration enhancers. The use of penetration enhancers is based on the disruption of the cell barriers by low molecular weight agents which can fluidize cell membranes [Kaji, H., et al., *Life Sci.*, 37:523–530 (1985)], open tight junctions [Inagaki, M., et al., *Rhinology*, 23:213–221 (1985)], and create pores in the cell membrane [Gordon, S., et al, *Proc. Natl. Acad. Sci. USA*, 82:7419–7423 (1985); Lee, V. H. L., et al, *Crtical Reviews in Therapeutic Drug Camer Systems*, CRC Press, 8:91–192 (1991)]. The use of these agents leads to a non-specific loss of barrier integrity and can lead to the absorption of a variety of large molecules which can be toxic to cells in vivo.

Protease inhibitors have been co-administered with proteins and peptides and have shown some limited activity in enhancing the absorption of these macromolecules in vivo [Kidron, M., et al., *Life Sci.*, 31:2837–2841 (1982); Takaroi, K., et al., *Biochem. Biophys. Res. Comm.*, 137:682–687 (1986)]. The safety and the long term effects of this approach have yet to be thoroughly investigated.

The prodrug approach is based on the modifications of peptides in a manner that will protect them from enzyme degradation and recognition. This has been achieved by substitution of the D-forms of amino acids in the structure of peptides, the blockage of vulnerable groups on peptides by amidation and acylation, the inversion of the chirality of peptides, and the introduction of conformational constraints in the peptide structure. The synthesis of prodrugs is only applicable to small peptides which have easily identifiable domains of activity.

Reduction in size is another feasible approach to increasing the transport potential of proteins. However, the active sites of proteins need to be mapped before size reduction can be attempted. In general, this approach is difficult to apply to the majority of proteins.

Carrier ligands, by virtue of their properties, can alter the cell uptake and transport characteristics of proteins and peptides. The essence of this approach is that a cell-impermeant protein or peptide is covalently attached to a carrier which is highly transported into cells. The mechanisms through which carrier ligands become endocytosed and transcytosed are important in deciding the suitability of the carrier for enhancing the transport of proteins and peptides. Macromolecular carriers are hydrophilic and do not partition into the membrane. Therefore, the transport of large polymeric carriers into the cells is mediated by the affinity of the carrier for the cell membrane. Generally, the uptake of a macromolecular conjugate starts with the binding to the cell membrane. The binding of the carrier to the cells can be specific (e.g. binding of antibodies to cell surface antigens), nonspecific (binding of cationic ligands or lectins to cell surface sugars), or receptor mediated (binding of transferrin or insulin to their receptors). Once the carrier is bound to the cell surface, it is taken up into vesicles. These vesicles then become processed stepwise and can be routed to several pathways. One pathway is the recycling of the vesicle back to the membrane from which it was invaginated. Another pathway, which is destructive to the conjugate, is the fusion with lysosomes. An alternative pathway, and one which leads to the transcytosis of the conjugate, is the fusion of the vesicle with the membrane opposite to the side from which it was derived.

The correct balance between the processes of endocytosis and transcytosis determine the delivery of a protein conjugate to its target. For instance, endocytosis may determine the extent to which a conjugate is taken up by the target cell, but transcytosis determines whether or not a conjugate reaches its target [Shen, et al., (1992), supra]. For successful absorption through the GI-tract, a conjugate must bind the apical membrane of the GI-mucosa, become internalized into the mucosal cells, be delivered across the cells, and finally become released from the basolateral membrane.

The current literature contains many reports which demonstrate that nonspecific carriers, such as polylysines [Shen, W. C. and Ryser, H. J. P., *Proc. Natl. Acad. Sci. USA*, 78:7589–7593 (1981)] and lectins [Broadwell, R. D., et al., *Proc. Natl. Acad. Sci. USA*, 85:632–646 (1988)], and specific carriers, such as transferrin [Wan, J., et al., *J. Biol. Chem.*, 267:13446–13450 (1992)], asialoglycoprotein [Seth, R., et al., *J. Infect Diseases*, 168:994–999 (1993)], and antibodies [Vitetta, E. S., *J. Clin. Immunol.*, 10:15S–18S (1990)] can enhance the endocytosis of proteins into cells. Reports dealing with transcytotic carriers for proteins are fewer, and very few studies have quantitated the transport of protein conjugates across cell barriers. Wheat germ agglutinin [Broadwell, et al., (1988), supra] and an anti-transferrin/methotrexate conjugate [Friden, P. M. and Walus, L. R., *Adv. Exp. Med. Biol.*, 331:129–136 (1993)] have been shown to be transcytosed across the blood brain barrier in vivo. Also, polylysine conjugates of horseradish peroxidase (HRP) and a transferrin conjugate of HRP have been shown to be transcytosed across cell monolayers in vitro [Wan, J. and Shen, W. C., *Pharm. Res.*, 8:S-5 (1991); Taub, M. E. and Shen, W. C., *J. Cell. Physiol.*, 150:283–290 (1992); Wan, J., et al., *J. Biol. Chem.*, 267:13446–13450 (1992), supra].

Fatty acids, as constituents of phospholipids, make up the bulk of cell membranes. They are available commercially and are relatively cheap. Due to their lipidic nature, fatty acids can easily partition into and interact with the cell membrane in a non-toxic way. Therefore, fatty acids represent potentially the most useful carrier ligands for the delivery of proteins and peptides. Strategies that may use fatty acids in the delivery of proteins and peptides include the covalent modification of proteins and peptides and the use of fatty acid emulsions.

Some studies have reported the successful use of fatty acid emulsions to deliver peptide and proteins in vivo [Yoshikawa, H., et al., *Pharm. Res.*, 2:249–251 (1985); Fix, J. A., et al., *Am. J. Physiol.*, 251:G332–G340 (1986)]. The mechanism through which fatty acid emulsions may promote the absorption of proteins and peptides is not yet known. Fatty acid emulsions may open tight junctions, solubilize membranes, disguise the proteins and peptides from the GI environment, and carry proteins and peptides across the GI-mucosa as part of their absorption [Smith, P., et al., *Adv. Drug Delivery Rev.*, 8:253–290 (1992)]. The latter mechanism has been proposed, but is inconsistent with current knowledge about the mechanism of fat absorption.

A more logical strategy to deliver proteins and peptides across the GI-epithelium is to make use of fatty acids as non-specific membrane adsorbing agents. Several studies have shown that a non-specific membrane binding agent linked to a protein can promote the transcytosis of a protein conjugate across cells in vitro [Wan, J., et al., *J. Cell. Physiol.*, 145:9–15 (1990); Taub and Shen (1992), supra]. Fatty acid conjugation has also been demonstrated to improve the uptake of macromolecules into and across cell membranes [Letsinger, R., et al., *Proc. Natl. Aced. Sci. USA*, 86:6553–4556 (1989); Kabanov, A., et al., *Protein Eng.*, 3:39–42 (1989)]. Nonetheless, there have been difficulties in conjugating fatty acids to peptides and proteins, including: (1) the lack of solubility of fatty acids in the aqueous solution for the conjugation reaction; (2) the loss of biological activity of peptides and proteins after fatty acid acylation; and (3) the lack of solubilitty of fatty acid-conjugated peptides in aqueous solutions [see, e.g., Hashimoto, M., et al., *Pharm. Res.*, 6:171–176 (1989); Martins, M. B. F., et al., *Biochimie*, 72:671–675 (1990); Muranishi, S., et al., *Pharm. Res.*, 8:649–652 (1991); Robert, S., et al., *Biochem. Biophys. Res. Commun.*, 196:447–454 (1993)].

It is an object of the present invention to provide methods and compositions for use in conjugating fatty acids to hydrophilic molecules and in improving the bioavailability of peptides and proteins.

SUMMARY OF THE INVENTION

In accordance with the present invention, fatty acid derivatives of sulfhydryl- or disulfide-containing compounds (for example, peptides, proteins or oligonucleotides which contain or are modified to contain sulfhydryl groups) comprising fatty acid-conjugated products with disulfide linkage(s) are employed for delivery of the sulfhdryl- or disulfide-containing compounds to mammalian cells. This modification markedly increases the absorption of the compounds by mammalian cells relative to the rate of absorption of the unconjugated compounds, as well as prolonging blood and tissue retention of the compounds. Moreover, the disulfide linkage in the conjugate is quite labile in the cells or in vivo and thus facilitates intracellular or extracellular release of the intact compounds from the fatty acid moieties. Reagents and methods for preparation of the fatty acid derivatives are also provided.

BRIEF DESCRIPTION OF THE DRAWINGS

The invention may be better understood with reference to the accompanying drawings, in which.

DETAILED DESCRIPTION OF THE INVENTION

Figure 1:
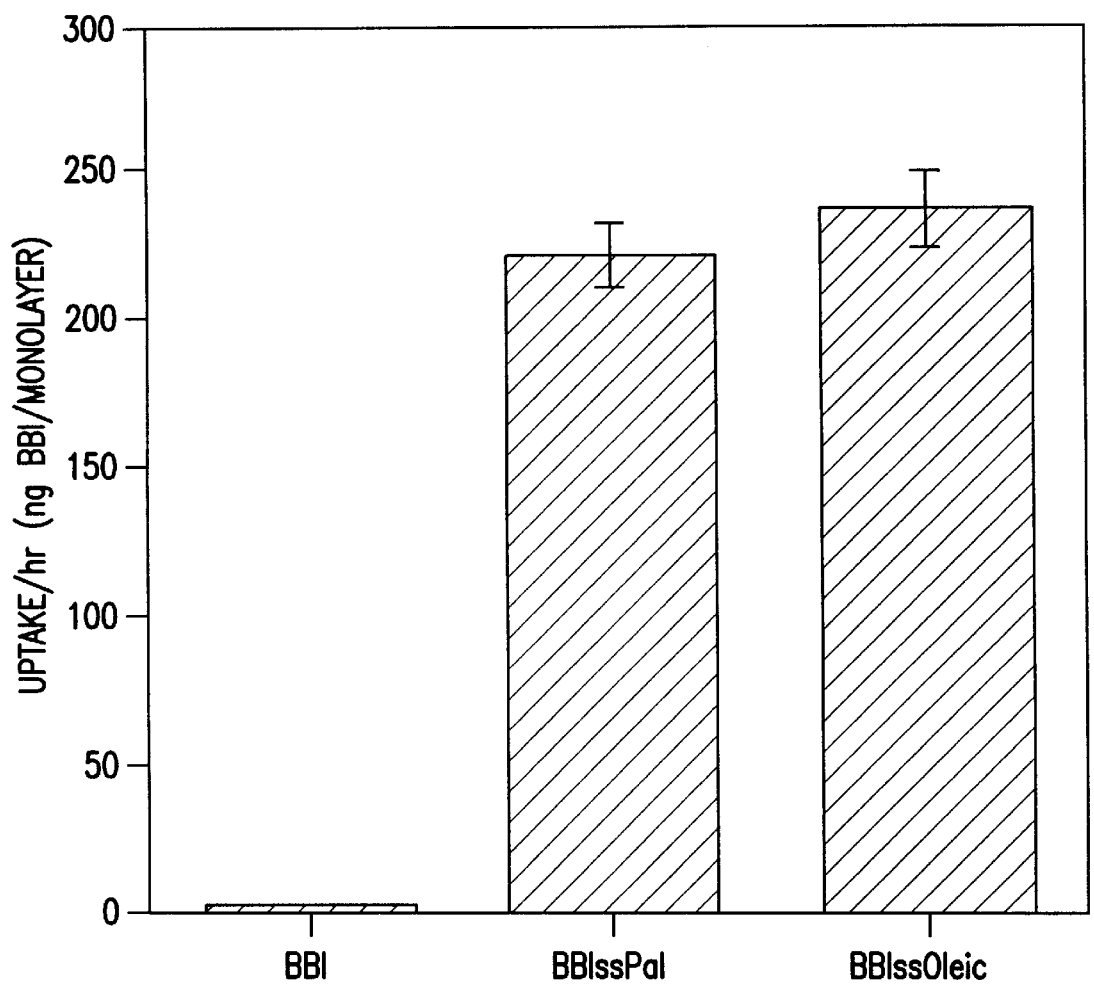
FIG. 1 is a bar graph illustrating the uptake of BBI, BBIssPal and BBIssOleic in Caco-2 cells.
Figure 2A:
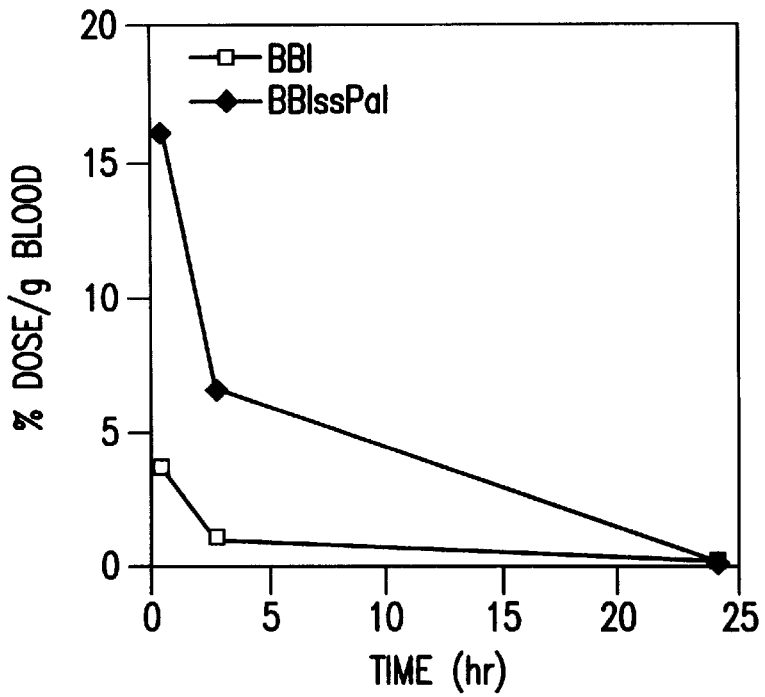
FIGS. 2A–2D are graphs which illustrate the biodistribution of BBI and BBIssPal in blood, kidneys, lungs and liver of CF-1 mice following iv-administration.
Figure 2B:
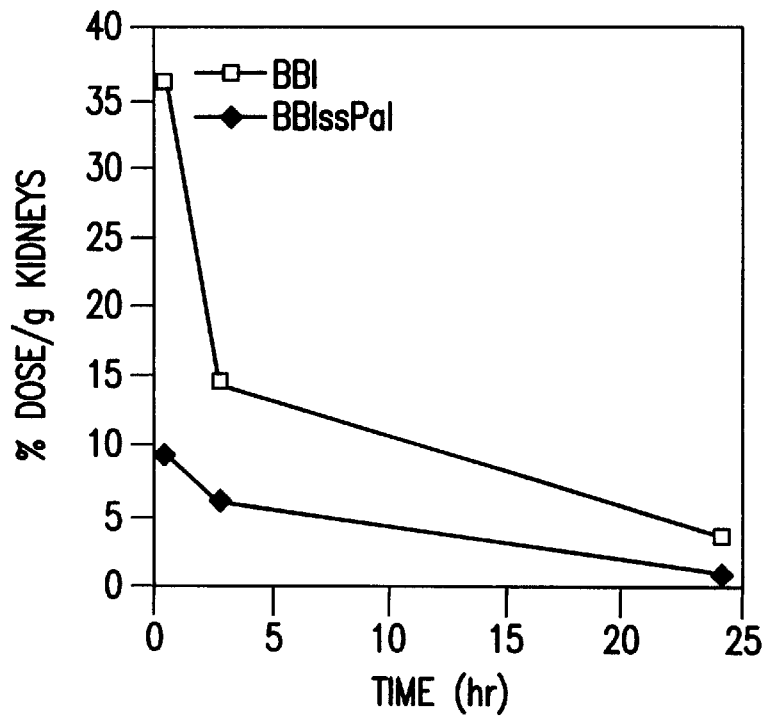
Figure 2C:
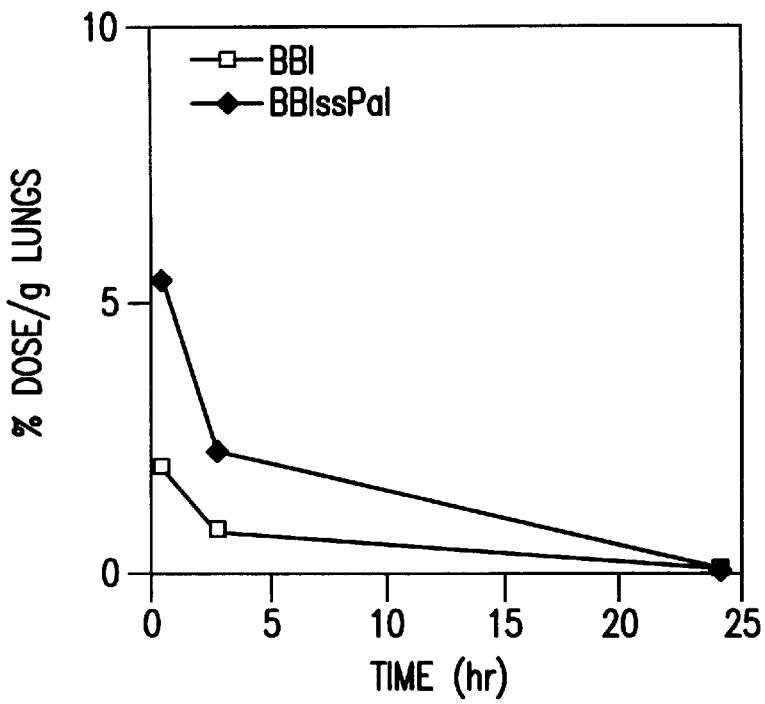
Figure 2D:
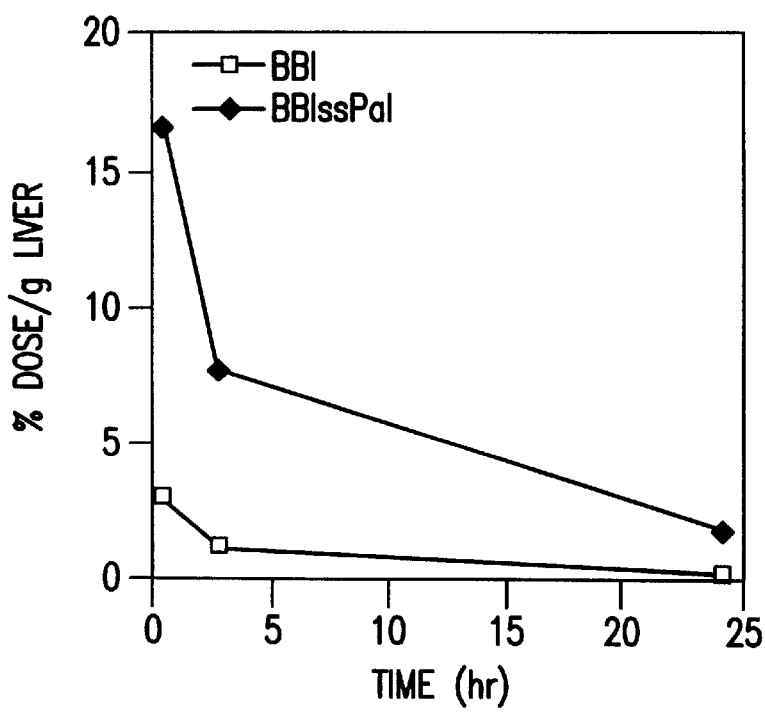
Figure 3A:
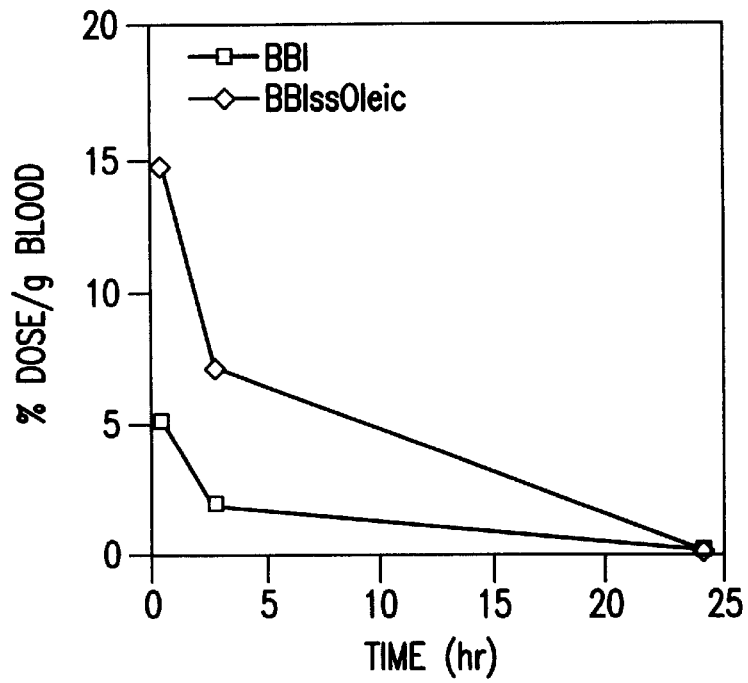
FIGS. 3A–3D are graphs which illustrate the biodistribution of BBI and BBIssOleic in blood, kidneys, lungs and liver of CF-1 mice following iv-administration.
Figure 3B:
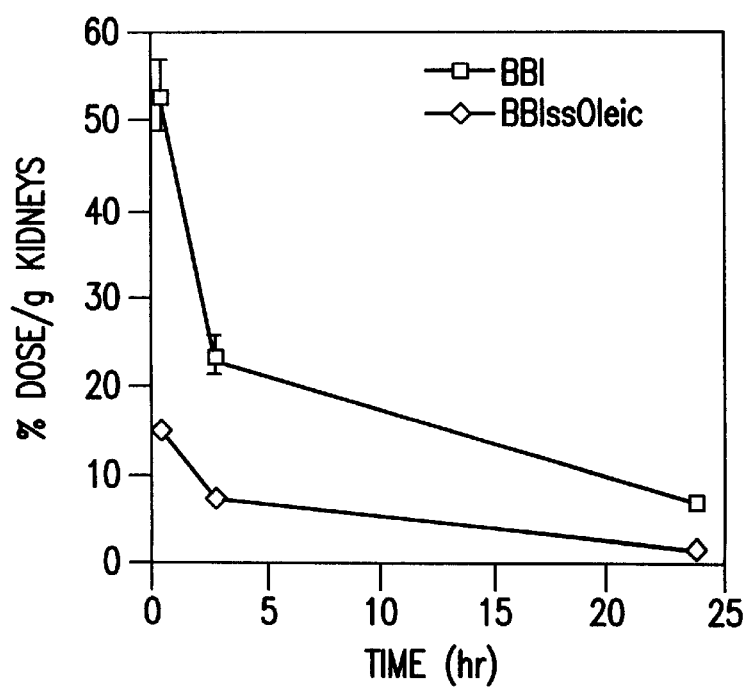
Figure 3C:
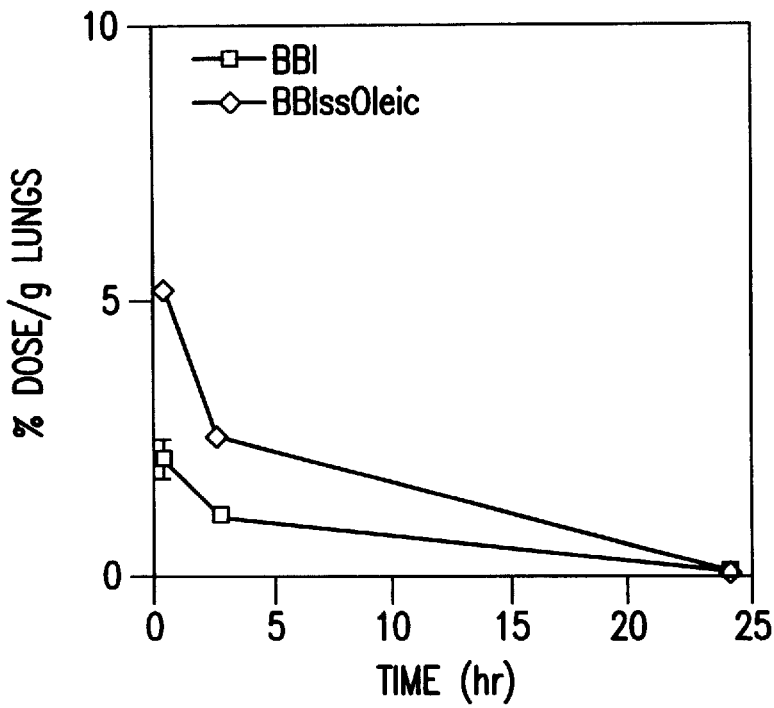
Figure 3D:
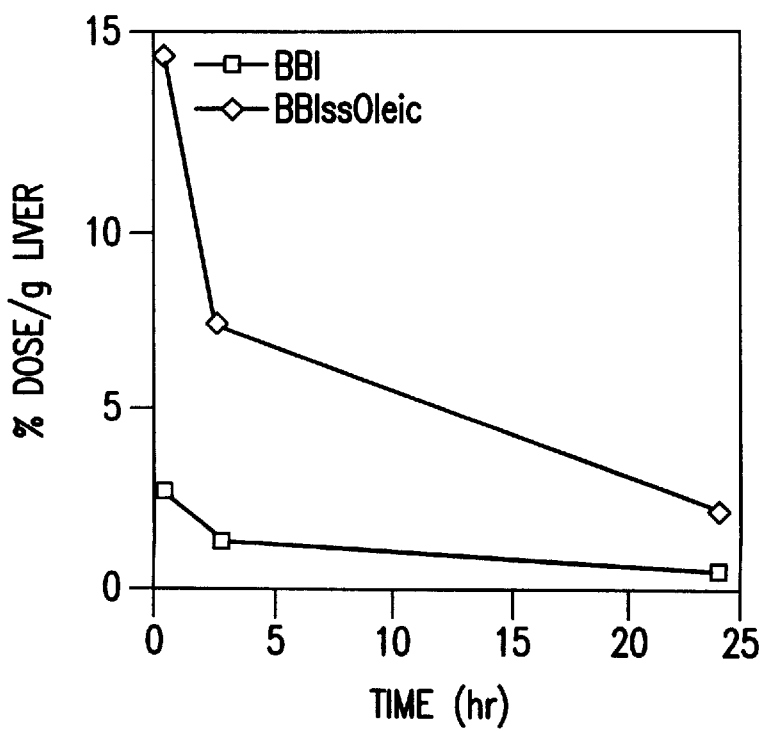

Pursuant to the present invention, a sulfhydryl-containing compound (for example, a biopolymer as hereinafter defined) is attached to a fatty acid derivative via a reversible, biodegradable disulfide bond. Such a conjugate would be expected to bind to the apical side of a cell membrane, reach the basolateral membrane of the GI-epithelium as a result of membrane transport and turnover, and may become released into interstitial fluid as the result of disulfide bond reduction.

Pursuant to one aspect of the present invention, there are provided conjugates of the general formula VI

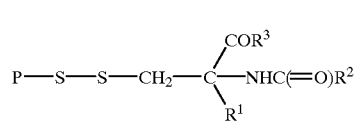

in which P is a residue derived from a sulfhydryl-containing compound; $R^1$ is hydrogen, lower alkyl or aryl; $R^2$ is a hydrophobic substituent (as hereinafter defined); and $R^3$ is hydroxy, a hyrdophobic substituent or an amino acid chain comprising one or 2 amino acids and terminating in $-CO_2H$ or $-COR^2$. These conjugates are particularly useful for increasing the absorption and prolonging blood and tissue retention of the sulfhydryl-containing compound PSH.

Pursuant to another aspect of the present invention, methods for increasing the absorption or prolonging blood and tissue retention in a mammal of a sulfhydryl-containing compound of the general formula PSH are provided, in which a conjugate of general formula VI is formed from the sulfhydryl-containing compound and the conjugate is then administered to the mammal (for example, as part of a pharmaceutical composition, e.g. in an aqueous solution or an oral dosage unit) wherein the conjugate is administered in an amount effective to achieve its intended purpose.

Pursuant to yet another aspect of the present invention, there are provided compounds of the general formula V

in which A is an aromatic activating residue (as hereinafter defined) and $R^1$, $R^2$ and $R^3$ are as previously defined. The compounds of general formula V are particularly useful in preparation of conjugates of general formula VI from sulfhydryl-containing compounds of general formula PSH.

Pursuant to still another aspect of the present invention, there are provided methods for forming conjugates of general formula VI from sulfhydryl-containing compounds of general formula PSH, which comprises reacting a compound of general formula PSH with a compound of general formula V. The reaction is typically carried out with an excess (e.g., a two-fold to a tenfold excess) of the compound of general formula V for a period of time of about 1 hour to about 24 hours at a A temperature of about 4° C. to about 37° C. in a suitable aqueous buffer solution (e.g., phosphate, bicarbonate or borate buffers). Preferably, the reaction is carried out in bicarbonate buffer, pH 8.

Pursuant to another aspect of the present invention, there are provided compounds of the general formula III

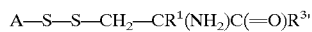

in which $R^3$ is hydroxy or an amino acid chain comprising one or two amino acids and terminating in $-CO_2H$ and A and $R^1$ are as previously defined. The compounds of general formula III are useful in preparing the compounds of general formula V. The compounds of general formula III are suitably prepared by reacting a compound of general formula II

with a compound of general formula A—S—S—A or A—S—S—A', in which A' is different from A and is an aromatic activating residue. These reactants are either commercially available [e.g., 2,2'-dithiopyridine and 5,5'- dithiobis (2-nitrobenzoic acid)] or may be prepared by routine synthetic procedures well known to those skilled in the art.

Pursuant to still another aspect of the present invention, there are provided methods for preparation of compounds of general formula V in which $R^2$ is a hydrophobic substituent, wherein a compound of general formula III is reacted with an activated lipid group of general formula X—$O_2$C—B or X—OC—B, in which X is a lipid-activating group (as hereinafter defined) and B is part of a lipid group (as hereinafter defined). Compounds of general formula X—$O_2$C—B or X—OC—B may be readily prepared in a manner known per se.

For preparation of a compound of general formula III, in an exemplary procedure generally equal molar quantities of a compound of general formula II and a compound of formula A—S—S—A or A—S—S—A' may suitably be mixed in a polar organic solvent (e.g., ethanol). The product of general formula III may then suitably be isolated by crystallization from a nonpolar organic solvent (e.g., benzene). Of course, other suitable procedures would also be evident to those working in the field.

For preparation of X—$O_2$C—B or X—OC—B, a fatty acid may for example be reacted with: (a) N-hydroxysuccinimide and a carbodiimide reagent to form an H-hydroxysuccinimidyl active ester; (b) trifluoroacetic anhydride to form a fatty acid anhydride; or (c) thionyl chloride to form a fatty acid chloride. Alternative procedures may also suitably be employed to introduce these or other lipid-activating groups.

For purposes of the present invention, the terms "hydrophobic substituent" and "lipid-containing moiety" refers to either a lipid group per se or a hydrocarbon-based group (in particular, one or more amino acids) comprising a lipid group. Such hydrophobic substituents may comprise about 4 to about 26 carbon atoms, preferably about 5 to about 19 carbon atoms. Suitable hydrophobic groups together with the carbonyl to which they are attached in the formulae include, but are not limited to, fatty acid residues including myristyl ($C_{13}H_{27}$), palmityl ($C_{15}H_{31}$), oleyl ($C_{15}H_{29}$), stearyl ($C_{17}H_{35}$), and elaidyl ($C_{17}H_{33}$), as well as residues of steriods having carboxy groups including cholate, deoxycholate, 17-carboxyequilenin and 17-carboxyestrone.

By "aromatic activating residue" is meant a moiety which serves to make the disulfide group of the compounds of general formula V more labile to the displacement reaction with the sulfhydryl-containing compounds of general formula PSH (and thus, serves as a good leaving group). A presently preferred aromatic activating group is 2-pyridyl; other suitable aromatic activating groups include 4-nitrophenyl.

The term "lipid-activating group" refers for purposes of the present invention to a moiety which renders a carboxy-lipid group to which it is attached reactive with a compound of general formula III. A presently preferred lipid-activating group is N-hydroxysuccinimidyl ester; other suitable lipid-activating groups include acid chloride and acid anhydride.

While the present invention contemplates the preparation and use of conjugates of general formula VI comprising a wide range of compounds containing sulfhydryl groups, it is particularly advantageous to employ the methods and compositions of the present invention for preparation of conjugates comprising biopolymers. Biopolymers of interest include peptides, proteins, and oligonucleotides (as hereinafter defined). As would be readily apparent to those working in the field, biopolymers or thiolated biopolymers containing sulfhydryl groups may comprise a plurality of moieties corresponding in structure to the conjugates of general formula VI (i.e., groups having the structure of the compounds of general formula VI minus the moiety P).

For purposes of the present invention, the term "peptide" refers to amino acid chains comprising two to 50 amino acids and the term "protein" to amino acid chains comprising more than 50 amino acids. The proteins and peptides may be isolated from natural sources or prepared by means well known in the art, such as recombinant DNA technology or solid-state synthesis. It is contemplated that the peptides and proteins used in accordance with the present invention may comprise only naturally-occurring L-amino acids, combinations of L-amino acids and other amino acids (including D-amino acids and modified amino acids), or only amino acids other than L-amino acids. In order to form a conjugate of general formula I, the peptide or protein must bear at least one reactive thiol group. In many cases, the peptide or protein contains cysteine residues (an amino acid comprising a thiol group). A peptide or protein which does not contain a thiol group may be modified by procedures well known per se to those working in the field; in particular, well known thiolating agents [e.g., N-succinimidyl-3-(2-pyridyidithio)propionate (SPDP) and 2-iminothiolane (Traut's reagent)] may be routinely employed for this purpose.

The term "oligonucleotide" refers to chains comprising two or more naturally-occurring or modified nucleic acids, for example naturally-occurring or recombinant deoxyribonucleic acids (DNA) and ribonucleic acid (RNA) sequences. For formation of a conjugate in accordance with the present invention, the oligonucleotide must be modified by thiolating reactions so as to contain a sulfhydryl group for linking with the lipid-containing moiety. Such modifications may be routinely carried out in a manner known per se. For example, an oligonucleotide may be coupled to cystamine using carbodiimide and subsequently reduced by dithiothreitol to generate a free sulfhydryl group. Such oligonucleotide conjugates can be used to deliver therapeutically effective oligonucleotides in vivo or ex vivo, that is, the conjugate is contacted with the cells in vitro to effect transfection. The cells may then be administered to an animal to achieve the therapeutic purpose. Alternatively, the oligonuclotide conjugates may be used to enhance transfection of mammalian cells in vitro for production in vitro of valuable recombinant proteins.

Preferred oligonucleotides are antisense oligonucleotides. Antisense oligonucleotides are DNA or RNA molecules or derivatives of a DNA or RNA molecules containing a nucleotide sequence which is complementary to that of a specific mRNA. An antisense oligonucleotide binds to the complementary sequence in a specific mRNA and inhibits translation of the mRNA. There are many known antisense oligonucleotides and derivatives thereof. See, for example, U.S. Pat. Nos. 5,602,240, 5,596,091, 5,506,212, 5,521,302, 5,541,307, 5,510,476, 5,514,787, 5,543,507, 5,512,438, 5,510,239, 5,514,577, 5,519,134, 5,554,746, 5,276,019, 5,286,717, 5,264,423, as well as WO96/35706, WO96/32474, WO96/29337 (thiono triester modified antisense oligodeoxynucleotide phosphorothioates), WO94/17093 (oligonucleotide alkylphosphonates and alkylphosphothioates), WO94/08004 (oligonucleotide phosphothioates, methyl phosphates, phosphoramidates, dithioates, bridged phosphorothioates, bridge phosphoramidates, sulfones, sulfates, ketos, phosphate esters and phosphorobutylamines (van der Krol et al., *Biotech.* 6:958–976 (1988); Uhlmann et al., *Chem. Rev.* 90:542–585 (1990)), WO94/02499 (oligonucleotide alkylphosphonothioates and arylphosphonothioates), and WO92/20697 (3'-end capped oligonucleotides). Preferred antisense oligonucleotides include derivatives such as S-oligonucleotides (phosphorothioate derivatives or S-oligos, see, Jack Cohen, *Oligodeoxynucleotides, Antisense Inhibitors of Gene Expression*, CRC Press (1989)). S-oligos (nucleoside phosphorothioates) are isoelectronic analogs of an oligonucleotide (O-oligo) in which a nonbridging oxygen atom of the phosphate group is replaced by a sulfur atom. The S-oligos may be prepared by treatment of the corresponding O-oligos with 3H-1,2-benzodithiol-3-one-1,1-dioxide which is a sulfur transfer reagent. See Iyer et al., *J. Org. Chem.* 55:4693–4698 (1990); and Iyer et al., *J. Am. Chem. Soc.* 112:1253–1254 (1990).

In one preferred class of compounds of general formula VI, $R^1$ is hydrogen, $R^2$ is a hydrophobic substituent or lipid moiety and $R^3$ is —OH. This type of conjugate is suitably derived from cysteine. In another preferred class of conjugate in accordance with the present invention, $R^1$ is hydrogen, $R^2$ is —CH$_2$CH$_2$CH(NH$_2$)CO$_2$H or —CH$_2$CH$_2$CH(NHCO-lipid)CO-lipid and $R^3$ is —NHCH$_2$CO$_2$H or —NHCH$_2$CO-lipid in which at least one of $R^2$ and $R^3$ together with the attached carbonyl is a lipid residue. This type of conjugate is suitably derived from glutathione.

The synthesis of an exemplary compound of general formula VI (in which P is a protein) is illustrated in Scheme I. Of course, as would be readily appreciated by those skilled in the art, a variety of alternative synthetic schemes could also readily be developed.

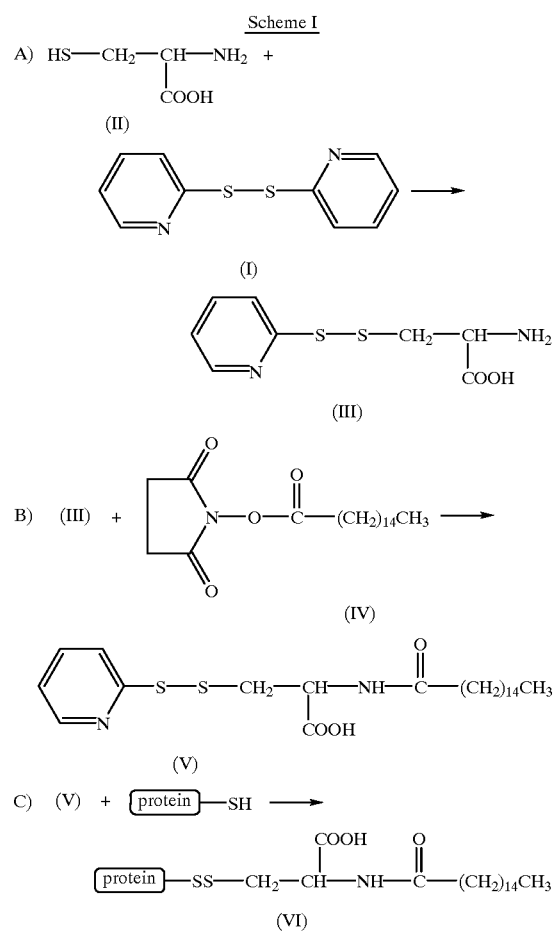

Another aspect of the invention presents fatty acid conjugates, represented by general formula (X), as shown below:

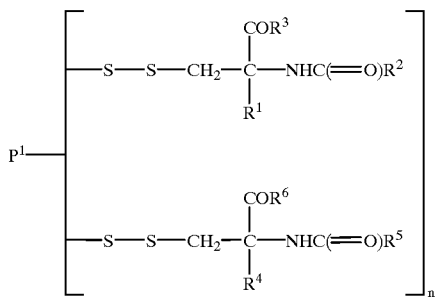

in which $P^1$ is a residue derived from a disulfide-containing compound which optionally may comprise a disulfide group linked to a hydrophobic group. Non-limiting examples of $P^1$ are peptides and proteins, or derivatives of compound (N) containing disulfide bonds, described further below. P and (N) are preferably drugs. Conjugate (X) is preferably an organic compound. n is an integer between 1 and 20, preferably no greater than 10, and more preferably no greater than 5. $R^1$, $R^2$ and $R^3$ are as previously defined for Formula VI. $R^4$ is hydrogen, lower alkyl or aryl; $R^5$ is a hydrophobic substituent (as previously defined); and $R^6$ is hydroxy, a hydrophobic substituent or an amino acid chain comprising one or two amino acids and terminating in —CO$_2$H or —COR$^2$. $R^1$ can be the same or different from $R^4$. $R^2$ can be the same or different from $R^5$. $R^3$ can be the same or different from $R^6$.

$R^2$ and $R^5$ together with the attached carbonyl are each preferably (1) a lipid-containing moiety comprising a lipid group; or (2) a lipid-containing moiety comprising a lipid group with an amino acid chain comprising one or two amino acids and terminating in —CO$_2$H. $R^3$ and $R^6$ are each preferably (1) an hydroxy group; (2) a hydrophilic group; or (3) an amino acid. A non-limiting example of $R^3$ and $R^6$ is glycine. Non-limiting examples of $R^2$ and $R^5$ are glutamic acid derivative, fatty acids and steroids such as deoxycholate and cholate.

The invention disclosed herein can be applied to many biologically-active agents including, but not limited to, sulfhydryl- or disulfide-containing proteins and peptides. Generally, these agents are poorly transported across biological barriers, rapidly eliminated from plasma, and susceptable to chemical and proteolytic degradation; therefore, their therapeutic applications are limited. The invention disclosed herein can overcome part or all of these limitations. Examples of sulfhyryl- or disulfide-containing proteins and peptides include, but not limited to, insulin [Czech, M. P., Ann. Rev. Biochem., 46, 359 (1977)], calcitonin [Brown, E. M., Aurbach, G. D., Vitam. Horm., 38, 236 (1980)], desmopressin [Vavra et al., J. Pharmacol. Exp. Ther., 188, 241(1974)], interferon-alpha, -beta, and -gamma [Stiem, E. R., Ann. Inter. Med., 96, 80–93 (1982)], interleukin-2, -3, -4, -6, and -11 [Kluth, D. C., Rees, A. J., Semin. Nephrol., 16, 576–82 (1996); Holyoake, T. L., Blood Rev., 10, 189–200 (1996)], G-CSF [Spiekermann, K. et al., Leukemia, 11, 466–78 (1997)], GM-CSF [Jonuleit, H. et al., Arch. Dermatol. Res., 289, 1–8 (1996)], human growth hormone [Strobl, J. S., Thomas, M. J., Pharmcol. Rev., 46, 1–34 (1994)], erythropoietin [Spivak, J. L., Semin. Hematol., 30, 2–11 (1993)], vasopressin [Schroder, E., Lubke, K., The Peptide, 2, 336–350 (1966)], octreotide [Sheppard, M. C., Stewart, P. M., Metabolism: Clinical and Experimental, 45, 63–64 (1996)], aprotinin [Haberland, G., McConn, R., Fed. Proc., 38, 2760–2767 (1979)], oxytocin [Nachtmann, F. et al., Anal. Prof. Drug Subst., 10, 563–600 (Florey, K. Ed., Academic Press, New York, 1981)], beta-TGF [Moses, H. L., Serra, R., Curr. Opin. Genet. Dev., 6, 581–6 (1996)], BDNF [Apfel, S. C., Kessler, J. A., Baillieres. Clin. Neurol., 4, 593–606 (1995)], bFGF [Bikfalvi, A. et al., Endocr. Rev., 18, 26–45 (1997)], PDGF [Hughes, A. D. et al., Gen. Pharmacol., 27, 1079–89 (1996)], TNF [Majno, P. E. et al., Swiss. Surg., 4, 182–5 (1995)], atrial natriuretic peptide [Nakao, K., Curr. Opin. Nephrol. Hypertens., 2, 45–50 (1993)], relaxin [Schwabe, C. et al., Recent Progr. Horm. Res., 34, 123–211 (1978)], amylin [Rink, T. J. et al., Trends. Pharmacol. Sci., 14,113–8 (1993)], deoxyribonuclease [Laskowski, The Enzymes, 2, 289–311 (Boyer, P. D., Ed., Acedamic Press, New York, 1971)] EGF [Carpenter, G., Curr. Opin. Cell. Biol., 5, 261–4 (1993)], hirudin [Markwardt, Methods Enzymol., 19, 924 (1970)], neocarzinostatin [Dedon, P. C., Goldberg, I. H., Chem. Res. Toxicol., 311–32 (1992)], hemoregulatory peptide [Paukovits, W. R. et al., Cancer Treat. Rev., 17, 347–54 (1990)] and somatostatin [Moss, R. L., Ann. Rev. Phsiol., 41, 617 (1979)].

A non-limiting example of conjugate (X) is

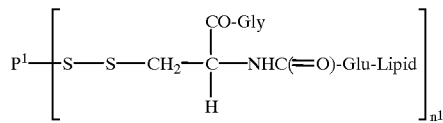

In the above formula, "Gly" denotes glycine, and "Glu" denotes glutamic acid. "$n^1$" is an even integer, preferably no greater than 10.

The preferred conjugate (X) has the following formula (wherein $R^1=R^4$, $R^2=R^5$ and $R^3=R^6$):

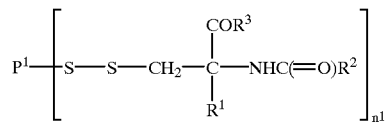

If the group $P^1$ contains a sulfhydryl group, it is possible to link a further hydrophobic group via a disulfide bond according to the present invention to give conjugates having an odd number of hydrophobic substituents, e.g. where $n^1$ is an odd number.

These conjugates are particularly useful for increasing the absorption and prolonging blood and tissue retention of the disulfide-containing compounds.

Pursuant to another aspect of the present invention, there are provided methods for increasing the absorption or prolonging blood and tissue retention in an animal, such as a mammal of a conjugate (X) which is administered to the animal as part of a pharmaceutical composition (for example, in an aqueous solution or an oral dosage form).

Pursuant to still another aspect of the present invention, there are provided methods for producing conjugate (X). Conjugate (X) is preferably formed from a compound containing one or more disulfide bonds and, optionally, one or more thiol groups.

The synthesis of exemplary compounds of general formula (X) is illustrated in Schemes II, III, and IV below (using conjugates of formula (D), (H), and (M) as examples of conjugate (X), respectively). Of course, as would be readily appreciated by those skilled in the art, a variety of alternative synthetic schemes could also readily be developed.

These schemes show the general methods for making di-fatty acid disulfide derivatives of general formula (X) from disulfide-containing compounds such as peptides and proteins, or compound (N) of Scheme IV which can be R—$NH_2$ or R—OH, wherein R is any organic moiety. Non-limiting examples of (N) are proteins, peptides, amino acids, nucleotides, nucleosides, carbohydrates and derivatives thereof as well as drugs. Non-limiting examples of (N) as drugs are antibiotics and hydrophilic drug molecules, e.g., acyclovir. These methods preferably allow for reversible modification of the di-fatty acid disulfide derivatives, i.e. conjugate (X), from disulfide-containing peptides or proteins, or compound (N).

The methods comprise reacting a disulfide-containing compound such as a peptide, protein, or compound (N) modified into a disulfide containing compound (such as compound (L) in Scheme IV), with compound of the general Formula V, described previously, i.e. A—S—S—$CH_2$—$CR^1$($NHCOR^2$)C(=O)$R^3$, to form conjugate (X). For purposes of illustration, the compound of Formula V is exemplified by compound (C) in Schemes II, III and IV. Based on the teaching disclosed herein, one skilled in the art would know the appropriate compound with the general Formula V to produce a desired conjugate (X). If the disulfide-containing compound also contains one or more sulfhydryl groups, they may also be conjugated to the hydrophobic group thus giving compounds with additional hydrophobic groups which may be odd or even depending on the number of sulfhydryl groups.

Conjugate (X) may be converted to the original disulfide molecules or compound (N) upon reaching blood or tissues. These methods and conjugate (X) overcome major limitations on peptide, polypeptide, protein, and organic compound (N) drug formulations, by improving the in vivo permeability, stability, and bioavailability of the peptide, protein, and organic compound (N), which may serve as drugs. Compared to unmodified peptide, protein, and organic compound (N), conjugate (X) (e.g., fatty acid-peptide conjugates or fatty acid-drug conjugates) have improved in vivo absorption, e.g., gastrointestinal absorption (e.g., when they are orally administered) and in vivo sustained release (e.g., when they are subcutaneously injected). The invention has the following advantages over the prior art: (1) the reaction can be carried out in aqueous conditions, (2) the products are generally water soluble, and (3) the product can be converted to the original peptide in the blood or tissues and thus a pharmacologically active drug can be regenerated.

For example, the methods may be used to prepare fatty-disulfide conjugates of cyclic disulfide-containing peptide drugs or homrones by using compound of the general Formula V (lipidizing agents). As shown in Scheme II below, a cyclic disulfide bond in a peptide or polypeptide (A) can be reduced to generate two free sulfhydryl groups (B). These sulfhydryl groups can react with fatty acid-disulfide derivatives such as N-acylcysteine pyridine disulfide (C) to yield a di-fatty aciddisulfide conjugated peptide or polypeptide derivative of the general formula (D). This derivative (D) can have an increased permeability to cells and a prolonged retention time in tissues. Preferably, it does not have any biological activity. When the derivative (D) is administered into a patients body and is reduced in vivo, derivative (D) can be converted to the original peptide or polypeptide (A).

SCHEME II

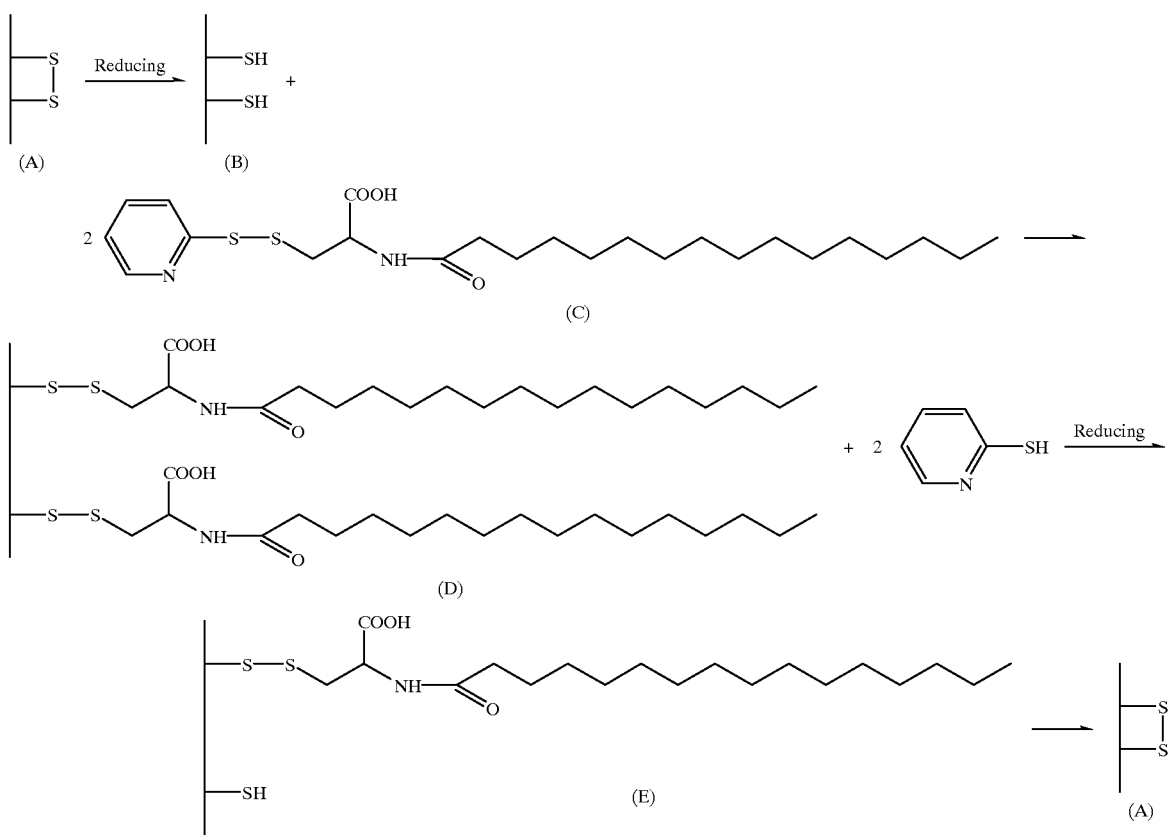

Scheme II   The preparation of a di-fatty acid disulfie conjugate (D) from a cyclic disulfide-containing peptide (A). (D) can be converted back to the original peptide (A), e.g., via the intermediate (E), upon reduction in the blood or tissues.

Scheme III illustrates another embodiment of the above invention: the preparation of fatty acid derivatives from disulfide-crosslinked two-chain polypeptides to produce the conjugate of the general formula (H).

SCHEME III

-continued

Scheme III  The preparation of a di-fatty acid disulfide conjugate (H) from a two-chain polypeptide with a cyclic structure consisting of two or more disulfide bonds (F). Similar to the reaction in Scheme II, (H) can be converted back to the original polypeptide (F) upon reduction.

Yet another method for preparing conjugate (X) is exemplified in Scheme IV which introduces the needed disulfide bonds into the starting compound (N) which does not have disulfide bonds or rings, or easily accessible disulfide bonds or rings. A cyclodisulfide-containing molecule, e.g., lipoic acid (J), is first conjugated to the compound (N) via an ester or an amide bond. After reducing, two disulfide fatty acid linkages can be formed (M). The di-fatty acid conjugate can be converted back to the original drug molecule (N) after reduction in the blood or tissues, and subsequent hydrolization by tissue enzymes. An example of Scheme IV is shown in Examples 20 and 21, below.

excess in molar concentration over the peptide or polypeptide; generally the ratio between the fatty acid and peptide or polypeptide for one cyclodisulfide is 3 to 1. In conjugate (X), the fatty acid is generally less than the peptide or polypeptide by weight. Thus, the relatively small amount of the fatty acid poses less toxic concern, unlike the administration of drug in lipid formulation, micelles, or liposomes.

The reaction is generally carried out in aqueous medium, at pH of preferably between pH 6 to 8, pH of 7.6 being preferred. The reaction is generally fast, going into completion at about 30 minutes or less to produce a stable conjugate (X). Conjugate (X) may be purified using methods known in

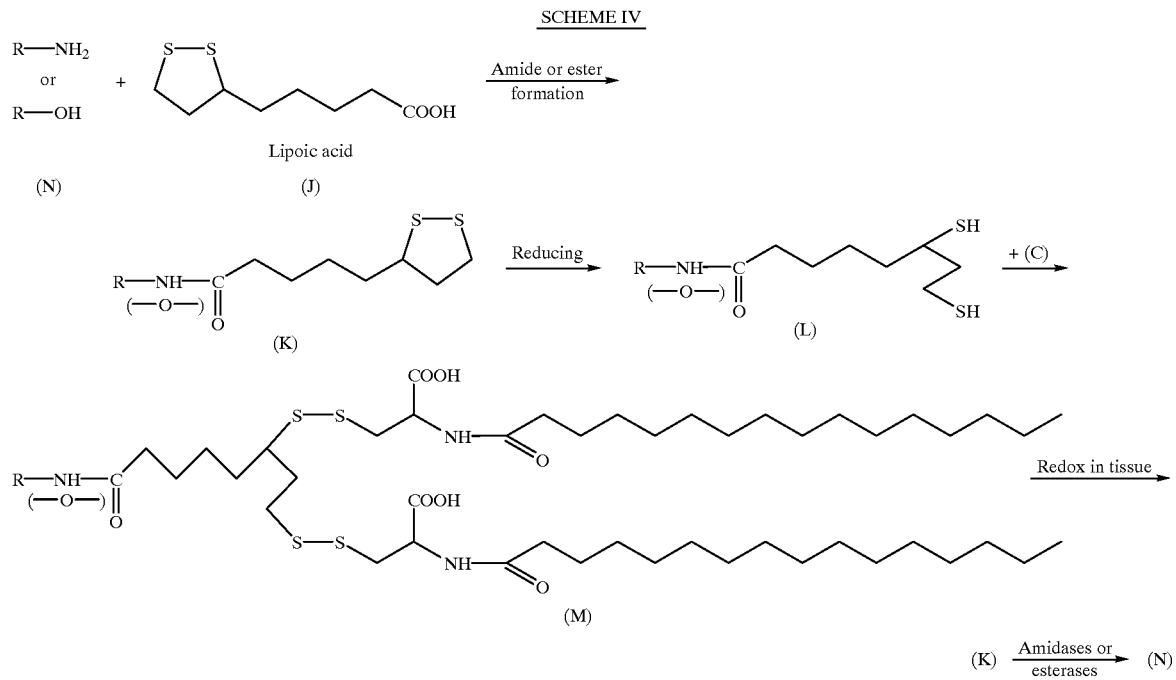

Conjugate (X) is desirable in that it is water soluble, it has lipophilic moiety or moieties which make it easier to be absorbed into a cell because it has cleavable linkage(s) which allow(s) for its sustained release in vivo. The peptide or polypeptide may have any number of amino acids and cyclic disulfide bonds. Modification of the peptide or protein typically takes place in aqueous solution such as PBS, or other buffers known in the art. The fatty acid that may be used generally have between 4 to 26 carbons, and more generally between 5 to 19 carbons. The non-limiting examples of the fatty acids are acetic acid (with 2 carbons); caproic acid (with 6 carbons); capric acid (with 10 carbons); lauric acid (with 12 carbons); myristic acid (with 14 carbons); palmitic acid (with 16 carbons); and stearic acid (with 18 carbons) (See Example 11, below). The method of Scheme II is generally useful for a peptide or polypeptide having between one to five cyclic disulfide bonds.

The reaction may be carried out at room temperature. At the start of the reaction, the fatty acid is generally at an the art for purifying proteins and peptides. The peptide or polypeptide in the conjugate confirmed by methods known in the art, such as by chromatography.

Examples of the peptides or proteins that can be modified according to Scheme II are: desmopressin (a nanopeptide with 9 amino acids and one cyclic disulfide ring, see Example 11, below); calcitonin (a peptide with 30 amino acids and one cyclic disulfide ring, see Example 17, below); octreotide (an octapeptide with one cyclic disulfide ring); oxytocin (a nanopeptide with one cyclic disulfide ring); and epidermal growth factor (a single polypeptide chain consisting of 53 amino acids with three cyclic disulfide rings). Insulin is an example of a polypeptide that can be modified according to Scheme II or III, since the insulin polypeptide consists of two chains (A- and B-chains) and a total of 51 amino acids with one cyclic disulfide ring in the A-chain (available for modification according to Scheme II) and one ring structure formed by two disulfide bonds (available for modification according to Scheme III) between the A-chain and B-chain.

In another embodiment of the invention, the fatty acids moiety of conjugate (X) may be substituted with other lipids, such as steroids (examples of which are shown in Examples 15 and 16, below). Group A in the reagent of general Formula V (i.e., A—S—S—CH$_2$—CR$^1$(NHCOR$^2$)C(=O) R$^3$)) is a good leaving group. A good leaving group is defined as a moiety which serves to make the disulfide group of the compound (A) of general formula V more labile to displacement reaction with sulfhydryl-containing compounds of general formula PSH, and thus serving as a good leaving group. Non-limiting examples of good leaving groups are p-nitro-o-ncarboxyl-thiophenol and thiopyridine. The definition of a leaving group can be found in most organic chemistry textbooks. For example, in page 241 of Cram and Hammond's *Organic Chemistry*, McGraw-Hill Book Co. (2nd ed., 1964), a leaving group "L" is defined as that "the C—L bond is ruptured in such a way that the pair of electrons which compose the bond becomes associated with L." Therefore, a moiety in an organic molecule is a good leaving group if it is capable of withdrawing the pair of electrons by either a high electronegativity or a resonance stability.

The fatty acid conjugates of the present invention are soluble in most buffer solutions in which proteins and peptides are soluble. In particular, any free carboxylic acid groups are charged at neutral pH and therefore improve the solubility of the conjugates. This greatly facilitates the formulation of the conjugates with suitable pharmaceutically-acceptable carriers or adjuvants for administration of the proteins or peptides to a patient by oral or other routes.

In the case where R$^1$ is not the same as R$^4$; R$^2$ is not the same as R$^5$; and R$^3$ is not the same as R$^6$; conjugate (X) may be made by conjugating a compound of the general formula VI$^1$ with a compound of the general formula VI$^2$ to form the compound of general formula (X). General formulae VI$^1$ and VI$^2$ are shown below:

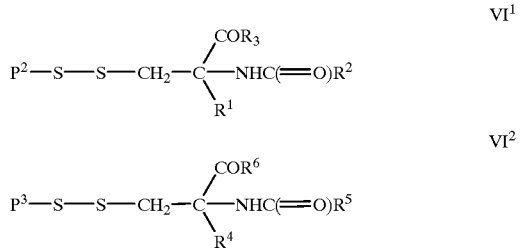

wherein p$^2$ and p$^3$ are residues derived from sulfhydryl-containing compounds, R$^1$, R$^2$, R$^3$, R$^4$, R$^5$ and R$^6$ are as previously described. It will be clear to one skilled in the art that compounds of general formulae VI$^1$ and VI$^2$ are examples of the compound with the general formula VI, described previously. Upon conjugation, P$^2$ and P$^3$ become P$^1$. Preferably, P$^1$, P$^2$ and P$^3$ are proteins or peptides, thus one skilled in the art may perform the synthesis by modifying peptide or protein conjugation methods known in the art.

It is a particular advantage in accordance with the present invention that the disulfide linkage between the fatty acid moiety and the peptide or protein may readily be reduced. Therefore, the active peptide or protein molecules are released in intact form inside the target tissues or cells. Furthermore, the fatty acid moiety of the conjugates comprises only amino acids and lipid molecules which are not toxic to mammals, in particular humans.

The pharmaceutical compositions of the present invention may be administered by any means that achieve their intended purpose. For example, administration may be by oral, parenteral, subcutaneous, intravenous, intramuscular, intra-peritoneal, transdermal, intrathecal or intracranial routes. The dosage administered will be dependent upon the age, health, and weight of the recipient, kind of concurrent treatment, if any, frequency of treatment, and the nature of the effect desired.

Compositions within the scope of this invention include all compositions wherein the compounds of the invention are contained in an amount effective to achieve their intended purpose. While individual needs vary, determination of optimal ranges of effective amounts of each compound is within the skill of the art.

In addition to administering the lipidized compounds of the invention as a raw chemical in solution, the compounds may be administered as part of a pharmaceutical preparation containing suitable pharmaceutically acceptable carriers comprising excipients and auxiliaries which facilitate processing of the compounds into preparations which can be used pharmaceutically. Suitable formulations for parenteral administration include aqueous solutions of the compounds in water-soluble form. In addition, suspensions of the compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers.

The compounds of the invention may also be combined with a lipophilic cationic compound which may be in the form of liposomes. The use of liposomes to introduce nucleotides into cells is taught, for example, in U.S. Pat. Nos. 4,897,355, 4,394,448 and 5,635,380. See also U.S. Pat. Nos. 4,235,871, 4,231,877, 4,224,179, 4,753,788, 4,673, 567, 4,247,411, 4,814,270 for general methods of preparing liposomes comprising biological materials. In a preferred embodiment, a metholic solution of dimyristoyl phosphatidyl choline, cholesterol and stearylamine (7:2:1) are evaporated to obtain a dry film. The film is hydrated in Tris® buffer containing appropriate amount of lipidized compound, followed by probe sonication.

The invention may be better understood with reference to the accompanying examples, which are intended for purposes of illustration only and should not be construed as in any sense limiting the scope of the invention as defined in the claims appended hereto.

EXAMPLES

Example 1

Synthesis of N-palmityl-2-pyridyldithiocysteine (Pal-PDC)

An ice-cold solution of L-cysteine (I) (3.0 g) in ethanol (50 ml) was added dropwise to a stirred solution of 2,2-dithiopyridine (II) (7.5 g) in ethanol (30 ml), and the reaction was allowed to proceed at 25° C. for 18 hr. The solution was centrifuged in order to remove any precipitate, and the supernatant was reduced in volume to 40 ml using a rotary evaporator. Subsequently, the reaction mixture was added dropwise to 400 ml of ice-cold benzene. PDC (III), which crystallized in benzene, was isolated by filtration, redissolved in 40 ml of ethanol, and then recrystallized in 400 ml of ice-cold benzene as described above. The recrystallized product was isolated by filtration, dried under vacuum overnight, and finally stored at −20° C. in a desiccator.

PDC (100 mg) (III) was dissolved in 5 ml of DMF and mixed with 100 μl of triethylamine, and the resultant suspension was reacted with the N-hydroxysuccinimide ester of palmitic acid (IV) (250 mg) in DMF (5 ml) at 25° C. for 24 hr, during which time the suspension turned clear. This solution was diluted with 40 ml of ice-cold water, pH 3.0, and the precipitate, which contained Pal-PDC (V) and palmitic acid, was isolated by centrifugation at 10000 rpm for 30 min. Pal-PDC (V) was separated from palmitic acid by suspension of the precipitate in water, pH 7.0, which dissolved Pal-PDC (V), but not palmitic acid. Pal-PDC (V) was purified further using two more steps of acid precipitation as described above.

Example 2

Synthesis of Conjugates

Unless otherwise stated, all the final reagents used in the conjugation steps (Pal-PDC and PDC) were analyzed using silica-coated thin layer chromatography (TLC) plates containing fluorescent indicators. These plates were not activated by heating prior to any of the analyses. For the routine analysis of the reagents synthesized, 5 μl of an ethanolic solution containing the reagent (5 mg/ml) was applied to the plates. Subsequently, the plates were developed in solvent chambers, equilibrated with the mobile phase. Once the solvent front had travelled a sufficient distance, the plates were removed, dried, and studied under a UV-lamp. Positions of the spots were marked on the plates immediately, and a drawing of the plate and the spots was made. The Rf value for each spot visualized was calculated and recorded. The composition of the mobile phases used in the analyses were adjusted to provide optimum separation of the reagent spots.

For purposes of illustration, conjugates of BBI were synthesized. BBI is a hydrophilic protein which has low uptake into cells and is not orally bioavailable. In addition, BBI is stable in the GI tract and resists degradation by the mammalian proteases in the gut [Yavelow, J., et al., *Cancer. Res.*, 43:2454s–2459s (1983)]. The use of BBI for chemoprevention can be accepted only if an orally absorbable form of BBI can be developed.

BBI (20 mg) was dissolved in 1 ml of a sodium bicarbonate solution (0.3 M, pH.8.0) and reacted with SPDP (5 mg/100 μl of DMF) for 2 hr at 25° C. After purification of BBI-PDP using Sephadex® G50 gel-filtration chromatography, the PDP-derivatization of BBI was estimated by measuring the release of the thiopyridine moiety after reduction of BBI-PDP with dithiothreitol (DTT). Using this procedure, approximately 4 amino groups per BBI molecule were modified with SPDP. The level of derivatization of BBI could be controlled by adjusting the pH of the reaction buffer; the modification of BBI could be adjusted from one amine group per BBI molecule when the reaction was carried out at pH 7, to 4.5 amine groups modified when the reaction was carried out at pH 8.5.

BBI-PDP (20 mg) in PBS (1 ml, pH 5.0) was reduced with DTT (25 mM) for 30 min and subsequently eluted from a Sephadex® G50 column. The sulfhydryl-containing BBI fractions, which eluted at the column void volume, were identified using Elman's reagent, and then reacted with a 3-fold excess (per sulfhydryl group on BBI) of Pal-PDC (V) in PBS, pH 7.0, for 16 hrs at 4° C. The reaction mixture was then acidified to pH 3.0 using HCl (1 M) and left on ice for 30 min. The supernatant was analyzed separately using a Sephadex® G25 gel-filtration column. The precipitate, which contained the palmityl disulfide conjugate of BBI, BBIssPal (VI), and the excess reagent, was isolated by centrifugation, dissolved in DMF (2 ml), and eluted from a Sephadex® LH20 column using DMF. BBIssPal (VI) fractions, which eluted at column void volume, were isolated, dialyzed 3 times against 500 volumes of water, and then lyophilized. The yield of the conjugate using this procedure was approximately 80% (by weight). The conjugation of Pal-PDC to BBI was confirmed and quantitated after the conjugation of [3H]-labeled Pal-PDC (V) to BBI using identical conjugation conditions as the ones described above. Also, using an identical procedure, the oleic acid conjugated BBI (BBIssOleic) was synthesized.

Example 3

Transport of Conjugates

Human colon carcinoma cells (Caco-2) were detached from 25 cm² stock culture flasks using a 10 min incubation at 37° C. with 0.5 ml of a trypsin/EDTA solution (0.5% trypsin, 5.3 mM EDTA). The cells were then suspended in 5 ml of Dulbecco's minimum essential medium, supplemented with 15% fetal bovine serum (FBS), L-glutamine (1%), and essential amino acids (1%), and counted using a coulter counter.

Suspended Caco-2 cells in 1.5 ml of medium were seeded into the apical chamber of the transwells at a density of 0.5 million cells per insert. 2.5 ml of the medium was then added to the basal chambers of each transwell. The cells were allowed to attach for 2 days without disturbance and were then fed every other day until the experiments were performed. The cells were maintained for approximately 14–20 days prior to the experiments and were fed 24 hr before each experiment. The cell monolayers developed a transepithelial electrical resistance (TEER) of approximately 500–600 Ω) cm² within one week of the seeding and maintained this resistance for up to 21 days post-seeding.

Radioiodination of BBI and BBIssPal was carried out using the chloramine-T method [McConahey, P. C. and Dixon, F. J., *Meth. Enzymol.*, 70:221–247 (1980)]. Confluent, 14-day old cell monolayers were washed once with, and then incubated in, serum-free Dulbecco medium at 37° C. for 30 min. Subsequently, the incubation medium was replaced with serum free medium containing $^{125}$I-BBI (10 μg/ml), either as native-BBI or as BBIssPal or BBIssOleic, and the monolayers were incubated for a further 60 min at 37° C. The monolayers were then washed three times with ice-cold PBS, and then exposed to trypsin (0.5%, EDTA 5.3 mM) for 10 min at 37° C. The detached cells were transferred to tubes, isolated by centrifugation, washed three times using ice-cold PBS, assayed for accumulated radioactivity using a gamma counter, and finally assayed for cell protein using the published method [Lowry, O. H., et al., *J. Biol. Chem.*, 193:265–275 (1951)].

In some experiments the uptake of reduced $^{125}$I-BBIssPal into cells was determined. $^{125}$I-BBIssPal was reduced with DTT (50 mM) at 60° C. for 5 min followed by a further 25 min at 37° C. In control experiments, $^{125}$I-BBIssPal was exposed in medium to the same temperatures without being exposed to DTT.

The uptake of $^{125}$I-BBIssPal in the presence of BSA (fatty acid free) was determined as follows. $^{125}$I-BBIssPal was incubated with medium containing 0.1% BSA for 30 min at 37° C. before being added to the cell monolayers. In some uptake experiments, BSA was first mixed with a 3-fold molar excess of palmitic acid, and then incubated with the conjugates prior to the experiments. In the experiments where the uptake of $^{125}$I-BBIssPal was determined in medium containing FBS, the conjugates was simply added to the medium containing the required amount of FBS.

Confluent cell monolayers, 2 to 3 weeks old, and having a TEER value of approximately 500 Ω cm$^2$, were first incubated with Dulbecco's MEM containing 1% of FBS for 30 min at 37° C. Subsequently, the incubation medium was removed, and the $^{125}$I-BBI (10 µg/ml) conjugates in 1.5 ml of the medium was added to the apical chamber of the transwells. To the basal chamber, 2.5 ml of the medium was added and the transwells were incubated at 37° C. At predetermined times, the entire basal chamber medium (2.5 ml) from each transwell was removed and counted for radioactivity using a gamma counter. In each experiment, typically seven samples were taken at 1, 2, 3, 4, 5, 6 and 24 hr post-incubation. After the 24 hr samples were taken, the cell monolayers were rinsed three times with ice-cold PBS, cut out of the inserts, and counted for accumulated radioactivity using a gamma counter.

The integrity of the $^{125}$I-BBI conjugates transported across the monolayers was studied using Sephadex® G50 gel-filtration chromatography. Briefly, after the basal medium was sampled at 24 hr, 1.0 ml of the medium was centrifuged at 2000 rpm and then eluted from a G50 column (10 ml) using PBS; 1 ml fractions were collected and the fraction-associated radioactivity was determined using a gamma counter. Intact conjugates eluted at column void volume and fragments smaller than 1 kDa were eluted at or above the column volume.

The results of the uptake of $^{125}$I-BBI, either as the free protein or in conjugated form to palmitic acid, in the presence of different amounts of added FBS are shown in Table 1. When the conjugates were incubated with the cells in serum-free medium, the uptake of BBIssPal was approximately 140-fold higher than that of BBI. In the presence of medium containing 1% FBS, the internalization of BBIssPal was increased by 35-fold over that of BBI. Increasing the serum concentration further to 10%, caused a further decrease in the uptake of BBIssPal into the cells to only a 10-fold higher level than that of native-BBI. The internalization of BBIssPal into Caco-2 cells was reduced drastically in the presence of serum to 14% and 2.3% of that of the serum-free values for 1% and 10% FBS containing media, respectively.

TABLE 1

| | Uptake (ng BBI/mg of cell protein)/hr | | |
| --- | --- | --- | --- |
| | serum free | 1% FBS | 10% FBS |
| BBI | 3.9 ± 0.19 | 2.2 ± 0.17 | 1.3 ± 0.02 |
| BBIssPal | 540.0 ± 24.13 | 78.5 ± 3.41 | 12.9 ± 0.02 |

The cell monolayers were incubated with $^{125}$I-labeled conjugates at 10 µg/ml for 60 min at 37° C. The results presented are the average of three monolayers ±SEM. The uptake experiments were carried out in Dulbecco medium, in the presence and absence of added FBS.

Since the BBIssPal uptake into the cells was believed to be mediated by the palmitic acid ligands on the conjugate, the uptake of $^{125}$I-BBIssPal into Caco-2 cells before and after reduction with DTT was studied. Since the presence of serum in the incubation medium had an inhibiting effect on the uptake of the conjugates into the cells, the uptake was studied in serum-free medium. The results are shown in Table 2. The uptake of untreated $^{125}$I-BBIssPal into the cells was 80-fold higher than that of $^{125}$I-BBI. The exposure of $^{125}$I-BBI to DTT did not cause a reduction in the uptake. In contrast, the reduction of $^{125}$I-BBIssPal with DTT reduced the uptake of the conjugate in to the cells by approximately 80%. The reduction of BBIssPal with DTT causes the detachment of the palmitic acid from the conjugate. Hence, the uptake of $^{125}$I-BBIssPal was mediated by the hydrophobic palmitic acid ligand.

TABLE 2

| | Uptake (ng BBI/mg of cell protein)/hr | |
| --- | --- | --- |
| | Untreated | DTT-treated |
| BBI | 4.8 ± 0.00 | 5.2 ± 0.00 |
| BBIssPal | 381.7 ± 0.03 | 46.5 ± 0.00 |

The cell uptake of $^{125}$I-BBI, either as the native protein or as BBIssPal was determined before and after reduction with DTT (50 mM) for 5 min at 60° C. and 25 min at 37° C.

Bovine serum albumin (BSA) is known to be a carrier of fatty acids in vivo and contain hydrophobic regions which can tightly bind fatty acids. Since the uptake of $^{125}$I-BBIssPal was reduced in the presence of serum, the possibility that BBIssPal bound to BSA present in FBS was investigated. The cell uptake of $^{125}$I-BBIssPal and $^{125}$I-BBI in the presence of medium containing fat-free BSA or fatty acid-loaded BSA was studied, and the results are shown in Table 3. In the presence of BSA-free medium, the uptake of $^{125}$I-BBIssPal into the cells was 80-fold higher than that of BBI, as was expected from the results obtained in the previous experiments. When defatted-BSA (fatty acid-free BSA) (0.1%) was present in the medium, the uptake of $^{125}$I-BBIssPal was reduced by 82%, whereas the uptake of $^{125}$I-BBI was not affected. In the presence of fatty acid-loaded BSA (0.1%), which was produced by spiking fat-free BSA with a 3-molar excess of palmitic acid, the uptake of $^{125}$I-BBI was again not affected. Therefore, $^{125}$I-BBIssPal binds strongly to BSA and this binding is dependent on the number of fatty acids already bound to BSA.

TABLE 3

| | Uptake (ng BBI/mg of cell protein)/hr | | |
| --- | --- | --- | --- |
| | serum free | BSA | BSA/FA |
| BBI | 4.8 ± 0.00 | 4.8 ± 0.00 | 3.9 ± 0.00 |
| BBIssPal | 380.0 ± 0.03 | 69.7 ± 0.00 | 258.9 ± 0.00 |

The uptake experiments were carried out in Dulbecco medium, in the presence and absence of added fatty acid-free BSA (BSA) or fatty acid-loaded BSA (BSA/FA). The results of studies of the uptake of $^{125}$I-BBI, either as the native-BBI or in conjugated form to palmitic or oleic acid, in Caco-2 cells in the presence of serum-free medium are presented in FIG. 1. The results are shown as the average ng of BBI internalized ±SEM, n=3. The uptake of $^{125}$I-BBIssPal into the cells was approximately 100-fold higher than that of $^{125}$I-BBI. Similarly, the uptake of $^{125}$I-BBIssOleic into the cells was about 108-fold higher than $^{125}$BBI. The difference between the uptake of $^{125}$I-BBIssPal and $^{125}$I-BBIssOleic were significant.

Example 4

Biodistribution Assays

Female CF-1 mice, 2 to 3 weeks old, weighing 20–25 g each, with free access to food and water prior to the experiments, were used for the animal experiments. $^{125}$I-BBI (3 mg/kg), as native-BBI or as BBIssPal or BBIssOleic conjugate, was administered to the animals via the tail vein. At 0.5, 3, and 24 hr post-injection, 3 animals from each experiment group were sacrificed and their blood (200 μl), the kidneys, the lungs, and the liver were removed, rinsed in ice-cold PBS, and assayed for accumulated radioactivity. The weights of the organs were recorded and used to adjust the concentration of the conjugates in the organs.

In the iv-biodistribution studies, $^{125}$I-BBI (3 mg/kg), either as the native-BBI or as BBIssPal, was administered into the lower left quadrant of the abdominal cavity of each animal. The animals were then treated in the manner described for the iv-biodistribution studies.

The results of the biodistribution of BBI and BBIssPal following iv-administration are shown in FIG. 2 as the % dose accumulated per g organ ±SEM. The results indicated that while BBI was rapidly excreted from the body without attaining high blood levels, BBIssPal was accumulated in the blood at a relatively high level and was apparently more slowly removed form the circulation. The kidney biodistribution results indicated that while BBI was rapidly accumulated in the kidneys, BBIssPal was not. The liver accumulation of BBIssPal was approximately 5-fold higher than that of BBI, and BBIssPal levels remained high in the liver even at 24 hr post-injection. The lung accumulation of BBIssPal was also approximately 2-fold higher than that of BBI, but this result may have been caused by the residual blood present in the organ after its excision. Clearly, BBIssPal was retained longer and at a higher level in the blood and the liver. On the other hand, the kidney clearance of BBIssPal was about 4-fold lower than native-BBI.

The iv-biodistribution of BBI and BBIssOleic were also studied in CF-1 mice. The results are presented in FIG. 3 as the % dose accumulated per g of the organ "SEM, n=3, at 0.5, 3 and 24 hr. The biodistribution of BBIssOleic was very similar to BBIssPal. As was observed for BBIssPal, BBIssOleic had higher blood levels than BBI and was apparently more slowly cleared from the circulation. The blood levels of BBIssOleic were about 4-fold higher than those of BBI at the same time points. The kidney clearance of BBIssOleic was approximately 4-fold lower, and the liver accumulation approximately 4-fold higher than native-BBI. The retention of BBIssOleic in the liver was prolonged, with significant levels of the conjugate present in the liver even at 24 hr post-injection. The lung levels of BBIssOleic were about 2-fold higher than native-BBI levels, but the higher residual blood in the lungs could account for this observation.

Figure 4A:
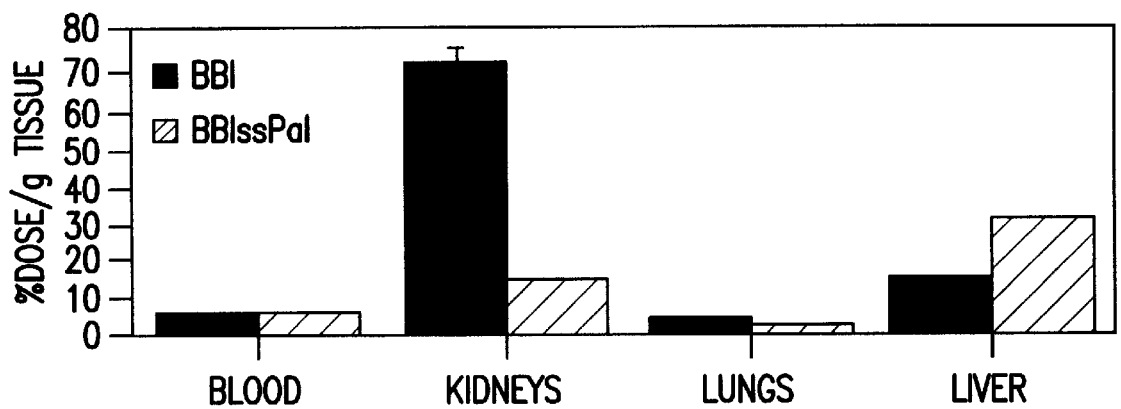
FIGS. 4A–4C are bar graphs which illustrate the biodistribution of BBI and BBIssPal in CF-1 mice following ip-administration.
Figure 4B:
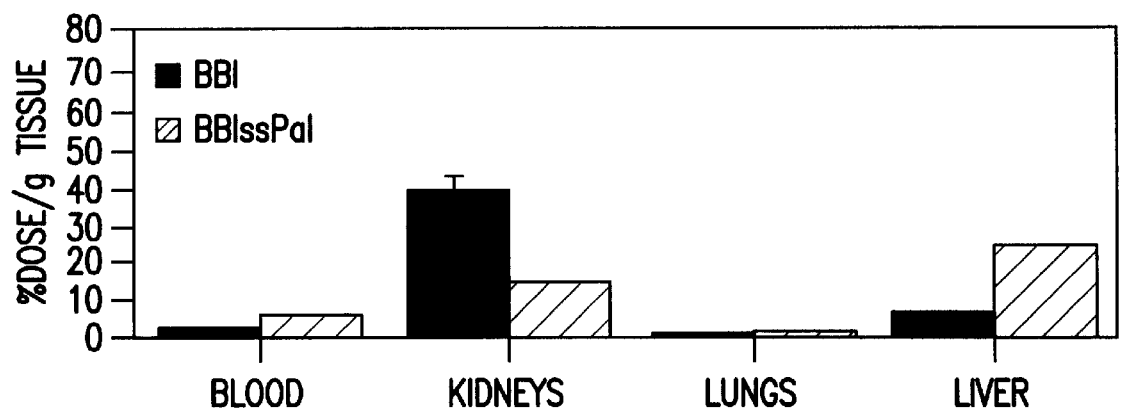
Figure 4C:
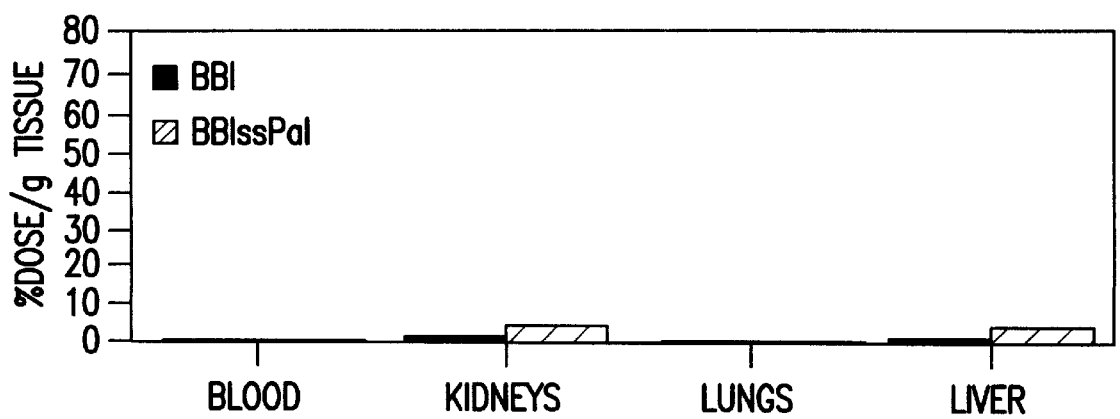

The iv-biodistribution of $^{125}$I-BBIssPal in CF-1 mice is shown in FIG. 4 as the average % dose accumulation per organ" range (bars) at 0.5 hr (FIG. 4A), 3 hr (FIG. 4B) or 24 hr post-injection (FIG. 4C). The kidney accumulation of $^{125}$I-BBIssPal was 4-fold lower than that of native $^{125}$I-BBI for the 0.5 and 3 hr time points. At 24 hr, $^{125}$I-BBIssPal levels were higher in the kidneys than $^{125}$I-BBI. The blood level of $^{125}$I-BBIssPal was similar to that of $^{125}$I-BBI at 0.5 hr, 1.5-fold higher than BBI at 3 hr, approximately 3-fold higher than BBI at 24 hr. The liver accumulation of $^{125}$I-BBIssPal was 1.5-fold higher than $^{125}$I-BBI at 0.5 hr, 2.5-fold higher at 3 hr, and about 4-fold higher at 24 hr. Relatively large amounts of $^{125}$I-BBIssPal were present in the liver and the kidneys at 24 hr.

Example 5

In Vitro Transformation Studies

Transformation assays were carried out using C3H 10T1/2(clone 8) cells according to the published recommendations [Reznikoff, C. A., et al., *Cancer. Res.*, 33:3239–3249 (1973); Reznikoff, C. A., et al., *Cancer. Res.*, 33:3231–3238 (1973)]. Stock cultures of mycoplasma-free cells were maintained by passing 50,000 cells per 75 cm$^2$ flask every seven days. Using this schedule, the cells were always passed approximately 2 days before reaching confluence. The stock culture was grown in Eagle's basal medium supplemented with 10% FBS, penicillin (100 units), and streptomycin (100 μg) and used for the transformation assays at passages of 9 to 14. The cells were passed by treating the stock cells with trypsin (0.1%) in PBS for 5 min and quenching the trypsin with 5 ml of the medium. This procedure was adapted to minimize spontaneous transformation in the stock cultures and maximize the plating efficiency in the petri dishes. The FBS stock used in the cultures was pre-screened to ensure that the serum was able to support the expression and the growth of the transformed cells.

For the transformation assays, C3H 10T1/2 cells (1000/dish) were seeded into 60 mm petri dishes and allowed to grow in a humidified 5% $CO_2$ atmosphere in Eagle's basal medium, supplemented with 10% FBS, penicillin (100 units), and streptomycin (100 μg), for 24 hr. Subsequently, the cells were initiated by treatment with 25 μl of the 3-methylcholanthrene (MCA) in acetone stock solution (0.25 mg/ml) to a final concentration of 1 μg/ml of MCA (5 μg/5 ml). The cells were allowed to grow in the presence of the carcinogen or solvent for 24 hr, and the medium in each dish was then replaced with fresh medium containing no carcinogen or solvent. The medium in the dishes was replaced twice per week for the first two weeks of the assay, and thereafter once a week for the remainder four weeks of the assay. In the experiments designed to determine the transformation inhibitory activity of the conjugates, the cells were maintained in the medium containing the conjugates (1 μg/ml) for the first three weeks of the assay; thereafter, the cells were maintained in medium containing no added conjugates.

Six weeks after the carcinogen treatment, the cells were inspected under a microscope for adherence to the culture dishes and were washed with PBS and then fixed in 100% methanol. The fixed monolayers were then stained with Giemsa stain. Twenty dishes per group were treated in each experiment. In addition to the test groups, all the transformation assays contained at least three other groups: negative control (not treated with carcinogen or solvent), acetone control (treated with 25 μl of acetone), and positive control [treated with MCA (1 μg/ml) in 25 μl of acetone]. The transformed foci (>3 mm in diameter) in the plates were studied under a microscope and classified according to published guidelines as types I, II, or III [Landolph, J. R., *Transfomatin assay of established cell lines: Mechanism and Application* (ed. Kakunaga, T., and Yamasaki, H.) IARC Scientific Publications, Lyon, France pp. 185–201 (1985)]. Briefly, type III foci were dense, multilayered, basophilic, areas of cell growth which stained to a deep blue color with Giemsa and had rough crisscrossed edges. Type II foci were also dense, multilayered, areas of cell growth, but were stained to a purple color with Giemsa and had smoother, more defined edges compared to Type III foci. Type I foci were not scored in the assay.

The plating efficiency (PE) of the cells was also studied in conjunction with each of the transformation assays. To determine the PE of the cells in the different treatment groups, cells (200 cells/dish) were seeded into three 60-mm petri dishes per experiment group and treated in the identical manner as the transformation assay cells. The cells in these assays were terminated at 10 days, fixed with 100% methanol, and stained with giemsa; the colonies of 50 cells or more visible under a microscope were then counted. The plating efficiency is defined as the (number of colonies/number of cells seeded)×100%.

The in vitro anti-transformation activity of BBI, BBIssPal, and BBIssOleic is shown in Table 4. BBI, either as the free protein or in conjugated form to palmitic or oleic acid, was added to the cultures at 1.0 μg/ml for the first three weeks of the transformation assay period starting immediately after the MCA treatment. MCA-treated cells were exposed to 3-methylcholanthrene, dissolved in 25 μl of acetone, at a concentration of 1 μg/ml for 24 hr. Acetone-treated cells were exposed to 25 μl of acetone for 24 hr only. The test groups were exposed to MCA for 24 hr and then to the conjugates for the first three weeks of the assay. Untreated cells were exposed to neither MCA nor acetone. Statistical analysis (Chi-square): Group 4 vs 3, $p<0.05$; Group 5 vs 3, $0.05<p<0.1$; Group 6 vs 3, $p<0.05$. Control, untreated cells reached confluence in the dishes about 14-days post-seeding formed well adherent, contact-inhibited monolayers. These dishes contained no transformed foci at the end of the assay period. The acetone treated cells also reached confluence and formed well-adherent monolayers 14 days post-seeding and contained no transformed foci. The MCA-treated dishes, however, contained morphologically transformed foci: 6 out of the 19 dishes scored contained type III foci. The BBI-treated group contained no transformed foci, indicating that BBI could prevent MCA-induced transformation in these cells. The BBIssPal-treated cells contained one type II focus out of the 20 dishes scored in the assay. The BBIssOleic treated cells contained no transformed foci. The PE of all the groups in this assay was between 20% to 25%. As demonstrated in Table 4, both BBIssPal and BBIssOleic retained the original biological activity of BBI.

isolated, and counted for accumulated radioactivity. The total counts in each experiments (medium+cell cpms) were determined, and the % of the total counts released at different times was determined.

In the transwell experiments, the conjugates were incubated with the apical side of the cells for 1 hr at 37° C. The transwells were then rinsed three times with ice-cold PBS and then reincubated with serum free medium. The release of the conjugates into the apical and the basal medium was chased for 24 hr by counting the entire basal or the apical medium at different times. The total counts obtained at the end of the chase period (transwells+media counts were added, and the release of the conjugates (% of total) at different times was calculated. To ensure that the counts obtained in the transwells at 24 hr were due to the presence of the conjugates in the cells and not non-specific binding to the plastic, the transwells were exposed to trypsin for 10 min, rinsed three times with ice-cold pbs, and subsequently counted for accumulated radioactivity.

Figure 5A:
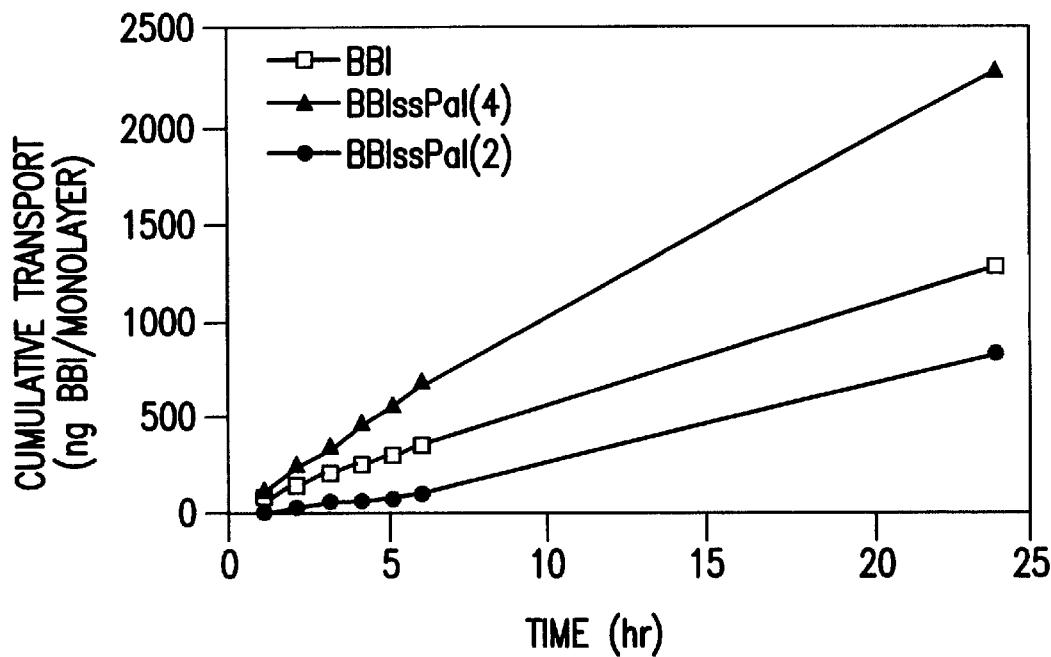
FIGS. 5A and 5B are a graph and bar graph, respectively, which illustrate the transcytosis and accumulation of BBI, BBIssPal(2) and BBIssPal(4) across and into Caco-2 cells.
Figure 5B:
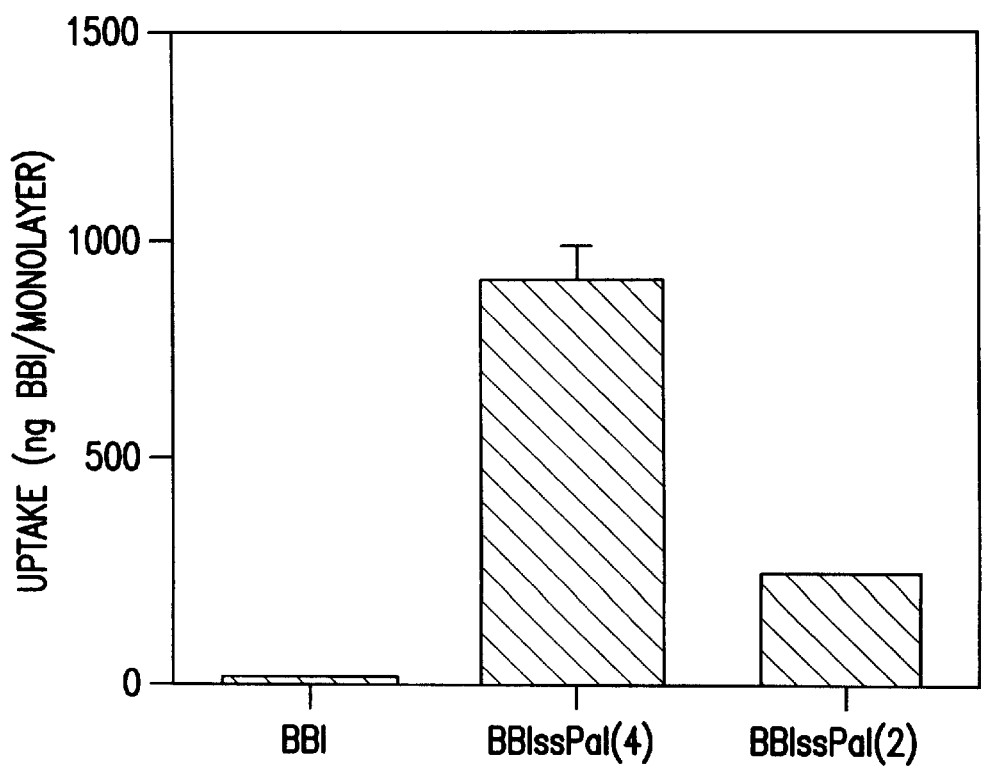
Figure 6:
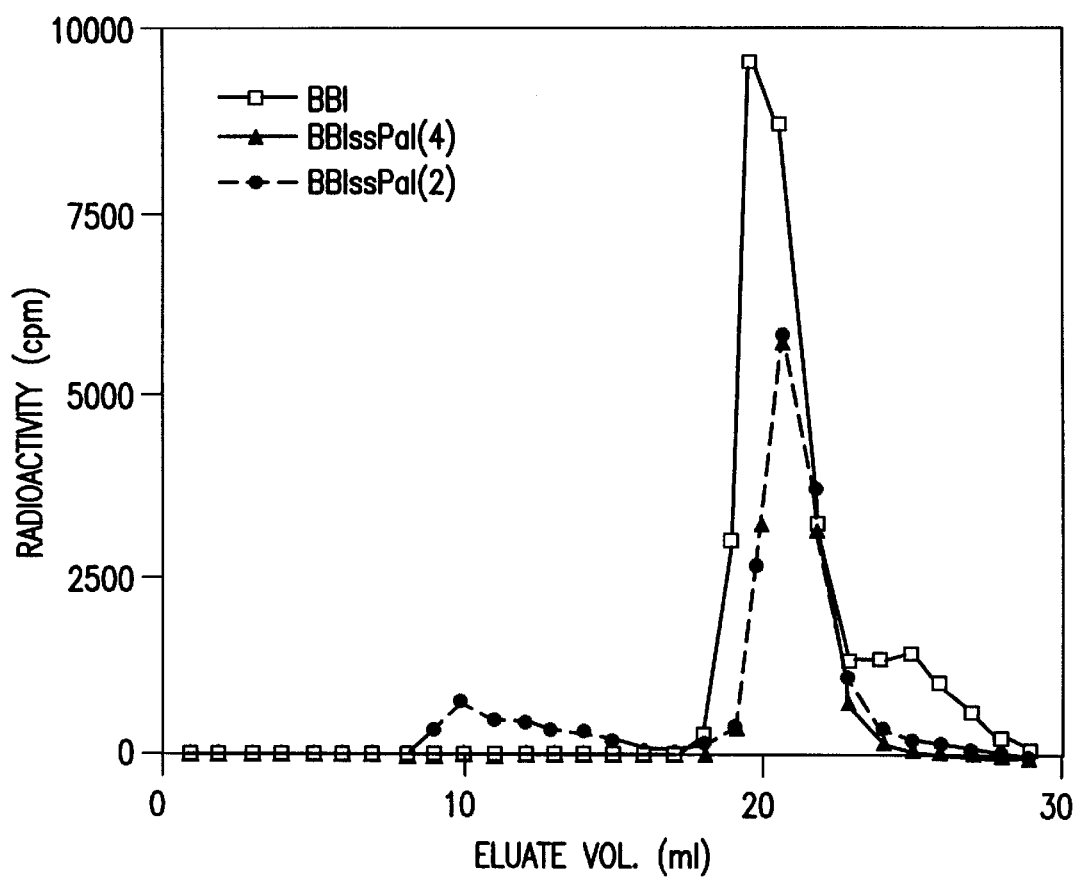
FIG. 6 is a graph which illustrates the results of Sephadex® G50 gel filtration analysis of basal medium from Caco-2 cells containing transcytosed BBI, BBIssPal(2) and BBIssPal(4).

BBI was modified with 2 or 4 palmitic acids, and the transport was determined in transwells. The cumulative transport of BBI, BBI modified with 4 palmitic acids [BBIssPal(4)], and BBI modified with 2 palmitic acids [BBIssPal(2)] in Caco-2 monolayers is shown in FIG. 5A; the results are expressed as BBI (ng/monolayer) ±SEM, n=3. The order of the transport extent was BBIssPal(4) >BBI>BBIssPal(2). The results of the internalization of the conjugates into the same cells is shown in FIG. 5B as the ng of BBI internalized per monolayer. As expected, BBIssPal (4) had the highest uptake into the cells, followed by BBIssPal(2) and BBI. The basal media obtained at 24 hr from the transwells was analyzed using a G50 column; the results are shown in FIG. 6. As had been observed before, neither BBI nor BBIssPal(4) was transcytosed across the monolayers. However, a small, but significant, amount of the

TABLE 4

| Treatment Group | Plating Efficiency (%) | No. of dishes with transformed foci/ No. of dishes | Fraction of dishes containing transformed foci |
|---|---|---|---|
| 1. Controls - untreated | 23 ± 1.5 | 0/20 | 0 |
| 2. Negative controls - acetone treated | 22 ± 2.0 | 0/20 | 0 |
| 3. Positive controls - MCA-treated | 21 ± 3.0 | 6/19 | 0.32 |
| 4. Test-MCA treated + BBI | 24 ± 2.0 | 0/20 | 0 |
| 5. Test-MCA-treated + BBIssPal | 23 ± 3.0 | 1/20 | 0.05 |
| 6. Test-MCA-treated + BBIssOleic | 24 ± 3.5 | 0/20 | 0 |

Example 6

Transport of Single- and Multiple-Conjugates

Studies on transport of apical membrane-bound $^{125}$I-BBIssPal were carried out using transwells and six-well plates. In the six-well plate experiments, $^{125}$I-BBI or $^{125}$I-BBIssPal (10 μg/ml) was incubated with Caco-2 cells in serum-free medium for 1 hr at 37° C. Subsequently, the cells were rinsed three times with ice-cold PBS and then divided into two groups. In the first group the internalization of the conjugates was determined after the trypsinization and isolation of the cells. In the second group, the cells were reincubated with serum-free medium and the release of the conjugates from the cells was chased for 24 hr; medium was removed at hourly intervals and counted for radioactivity. At the end of the chase period, the cells were trypsinized, basal media of BBIssPal(2) consisted of intact conjugate. This quantity consisted of between about 10 and about 20% of the total radioactivity present in the basal medium.

Example 7

Skin Absorption of BBIssPal

Freshly-prepared skins from hairless mice were mounted on small rings. To each mounted skin, a 5 μl sample of $^{125}$I-labeled BBI or BBIssPal at a concentration of 0.5 mg/ml was applied to an area of 0.38 cm$^2$. Two pieces of skin were used per treatment. The skins were kept at room temperature (23° C.) in a humidified environment. After 30 minutes, the surface of the skins was first rinsed carefully with PBS; subsequently, the skins were unmounted and soaked twice in 100 ml of PBS. The skins were then blotted with filter papers and counted in a gamma counter. The amount of BBI retained on the skins was calculated using the specific radioactivity of the labeled BBI or BBIssPal. The absorption of BBI and BBIssPal into the mouse skins was 0.14 and 1.6 $\mu g/cm^2$, respectively. This demonstrates that a more than 10-fold increase of BBI absorption into the skin was achieved when the polypeptide was modified using Pal-PDC.

Example 8

Synthesis of Palmitylated Horseradish Peroxidase (HRPssPal)

Ten milligrams of horseradish peroxidase (molecular weight 40,000; Sigma Chemical Company, St. Louis, Mo., USA, catalog number P 8375) in 0.5 ml of PBS was mixed with 2 ml of SPDP in 0.1 ml DMF at 25° C. for two hours. The reaction was terminated by dilution with 0.5 ml PBS, and dialyzed in 500 ml of PBS at 4° C. After 24 hours, the solution in the dialysis tube was removed, reduced by the addition of 50 $\mu$l of 1 M DTT, and separated by using a Sephadex® G-50 column. Fractions at the void volume of the column were pooled and mixed with a 10-fold molar excess of Pal-PDC in borate buffer, pH 9.6 at 25° C. for 4 hours. The reaction mixture was then dialyzed exhaustively at 4° C. for 3 days, and the final product was estimated to contain 10 palmitic acid residues per molecule of HRP. The HRP molecules retained approximately 20% of the original enzyme activity.

Example 9

Cellular Uptake of HRPssPal

Confluent monolayers of mouse fibroblasts L929 cells in 6-well culture cluster plates were incubated in serum-free medium with 30 $\mu$g/ml of HRP, either as the native form or as the palmitic acid conjugate (HRPssPal). After 1 hour at 37° C., monolayers were washed three times with PBS and then dissolved in 1 ml of 0.05% of Triton-X100. Cell-associated HRP was determined by measuring the enzymatic activity in each cell extract and the results converted to ng HRP per cell monolayer. Results indicated that cellular uptakes of HRP and HRPssPal were 7 and 229 ng HRP per cell monolayer, respectively. Therefore, a 30-fold increase in cell uptake was achieved by modification of HRP with Pal-PDC.

Example 10

Lipidization of Oligonucleotides

An antisense 21 mer oligonucleotide which is complementary to the mRNA of monoamine oxidase B is thiolated using the following procedure. The oligonucleotide is mixed with a two-fold molar excess of cystamine in the presence of a water-soluble carbodiimide reagent, EDC. The mixture is maintained at 25° C. for 2 hours and a two-fold molar excess to cystamine of DTT is added to reduce disulfide bonds. After separating the oligonucleotide from free cystamine and DTT using a Sephadex® G-25 column, a small amount of the thiolated oligonucleotide is reacted with Eliman's reagent and the concentration of sulfhydryl groups determined using the absorbance at 412 nm (assuming an $\epsilon$ of $1.36\times10^4$ $M^{-1}$). Subsequently, the number of sulfhydryl groups per oligonucleotide molecule is determined. The thiolated oligonucleotide is mixed in bicarbonate buffer, pH 8, with Pal-PDC in two-fold molar excess to the number of sulfhydryl groups in the oligonucleotide. The palmitylated oligonucleotide is purified using a Sephadex® G-25 column.

Example 11

Synthesis of Desmopressin-Fatty Acid Conjugates

Desmopressin (DP, 4 mg) was dissolved in 2 ml of PBS (pH 7.4) and treated with 74.8 ml of dithiothreitol (DTT, 0.1 M) at 37° C. The reaction was monitored by using TLC (solvent: butanol:water:acetic acid (4:5:1), upper layer). The reduction of the disulfide bond in DP was completed within 30 min, as indicated by the conversion of DP (Rf=0.15) to a single ultraviolet (UV)-absorbing spot (Rf=0.20) in the TLC. The DTT-reduced DP (dithiodesmopressin) was proceeded without further purification for the subsequent conjugation. The reduced DP solution was mixed with 2.24 ml of 10 mM Pal-PDC (10 mM, pH 7.6) for 30 min at 25° C. and, subsequently, acidified to pH 3 using HCl (1N). The precipitate formed in the acidified reaction mixture, which consisted of the palmityl disulfide conjugate of desmopressin (DP-P) and the excess reagent, was isolated by using centrifugation and re-dissolved in 1 ml of dimethylformamide (DMF). DP-P was subsequently purified by using a Sephadex® G 15 column (40 ml) using DMF as the eluant. The DP-P containing fractions at the void volume of the column were identified by TLC analysis (DP-P: Rf=0.24) and pooled. After the removal of the solvent under vacuum, 3.8 mg of purified DP-P was obtained.

In vitro conversion of DP-P to DP was demonstrated in the presence of DTT as the reducing reagent. Ten ml of DP-P (1 mg/ml, PBS) was treated with 5 ml of DTT (0.1 M) and was reacted at 37° C. TLC analysis of the resultant solution revealed the gradual disappearance of DP-P (Rf=0.24) with a concomitant regeneration of DP (Rf=0.15). After 1 hr, the conversion of DP-P to DP was completed.

DP conjugates linked to acetic, caproic, capric, lauric, myristic, or stearic acid were prepared by using similar procedures as described above, except that Pal-PDC was replaced by the respective fatty acid-PDC reagents.

Example 12

Effects of DP-P on Rats with Hereditary Hypothalamic Diabetes Insipidus

Figure 7A:
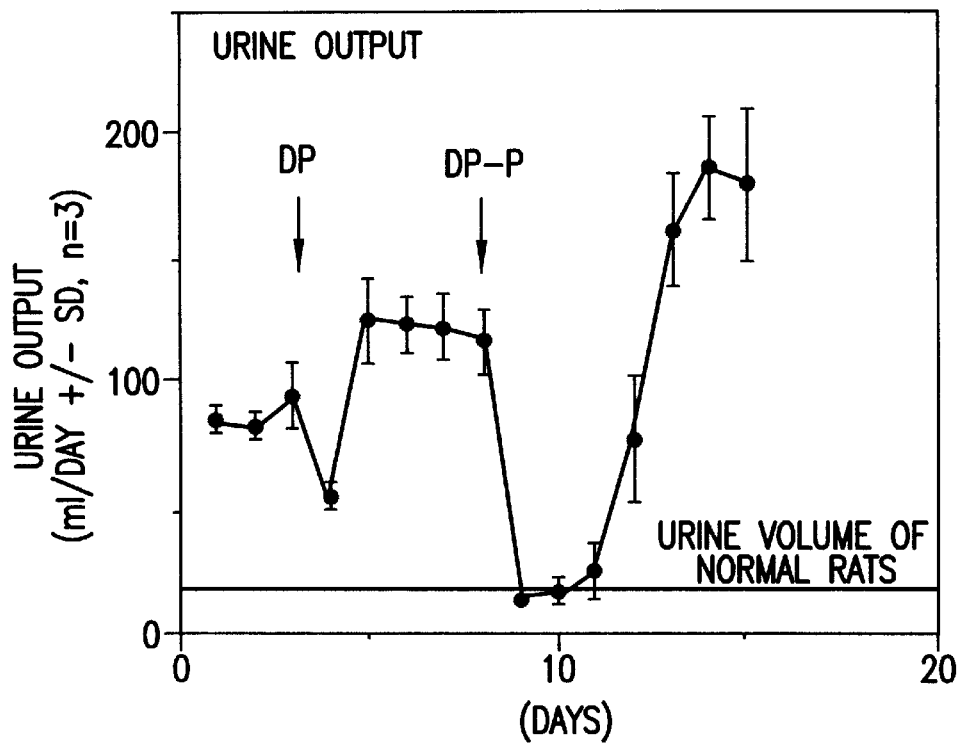
FIGS. 7A and 7B are graphs which present the effects of subcutaneously administered DP and DP-P on rats with diabetes insipidus, at a dose of 3.3 μg/kg: (7A) illustrates the urine output, (7B) illustrates the water intake.
Figure 7B:
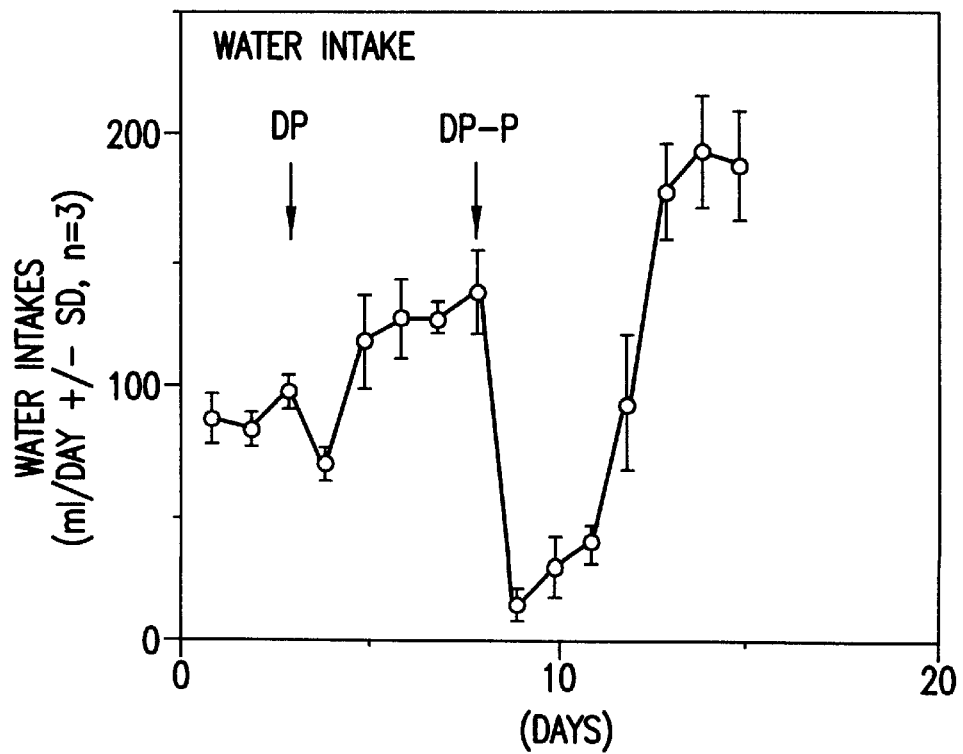

Brattleboro rats, which carry the hereditary disease of hypothalamic diabetes insipidus, were used to compare the effects of DP and DP-P for alleviating the disease symptoms, i.e., polyuria and polydipsia. A group of three Brattleboro rats were kept separately in three metabolic cages. Their body weight, water intake and urine output were measured every day. DP and DP-P were dissolved in 10% Liposyn® II (Abbott Laboratories, Abbott Park, Ill., USA) and injected subcutaneously (s.c.) to each rat at doses ranging from 0.02 to 20 $\mu$g/kg. FIG. 7 shows a typical response to the DP treatment at a dose of 3.3 $\mu$g/kg which maintained the rats symptom-free for less than one day. On the other hand, DP-P at the identical dose could maintain the rats symptom-free for more than 3 days, as indicated by the reduction of both water intake and urine output without significant change of the body weight.

Figure 8:
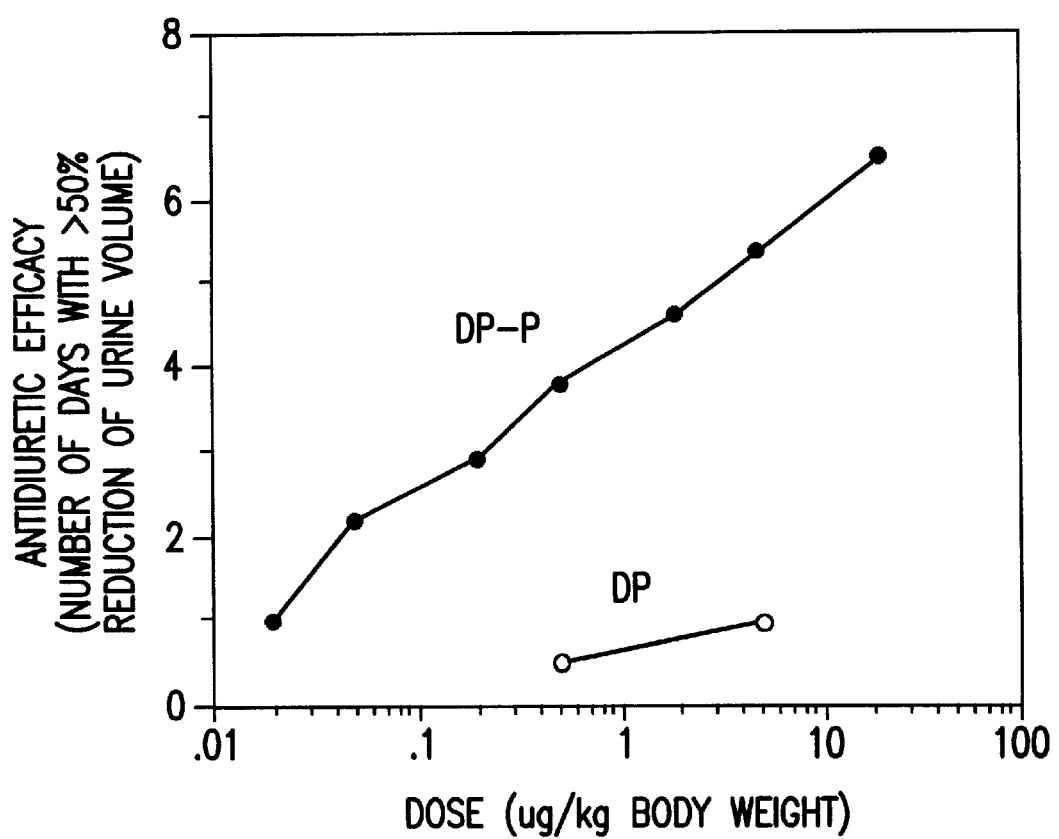
FIG. 8 is a graph which compares the efficacies of DP and DP-P as a single subcutaneous injection for the treatment of rats with diabetes insipidus at different doses.

In order to evaluate the dose-dependent responses to DP and DP-P in Battleboro rats, the effectiveness of anti-diuretic activity was defined as the length of time that a more than 50% reduction of the urine volume can be maintained in the treated animals. As shown in FIG. 8, DP-P was at least 250-fold more effective than DP when administered subcutaneously for the treatment of diabetes insipidus, because a similar effect was obtained with 0.02 μg/kg of DP-P and 5 μg/ml of DP.

Example 13

Figure 9:
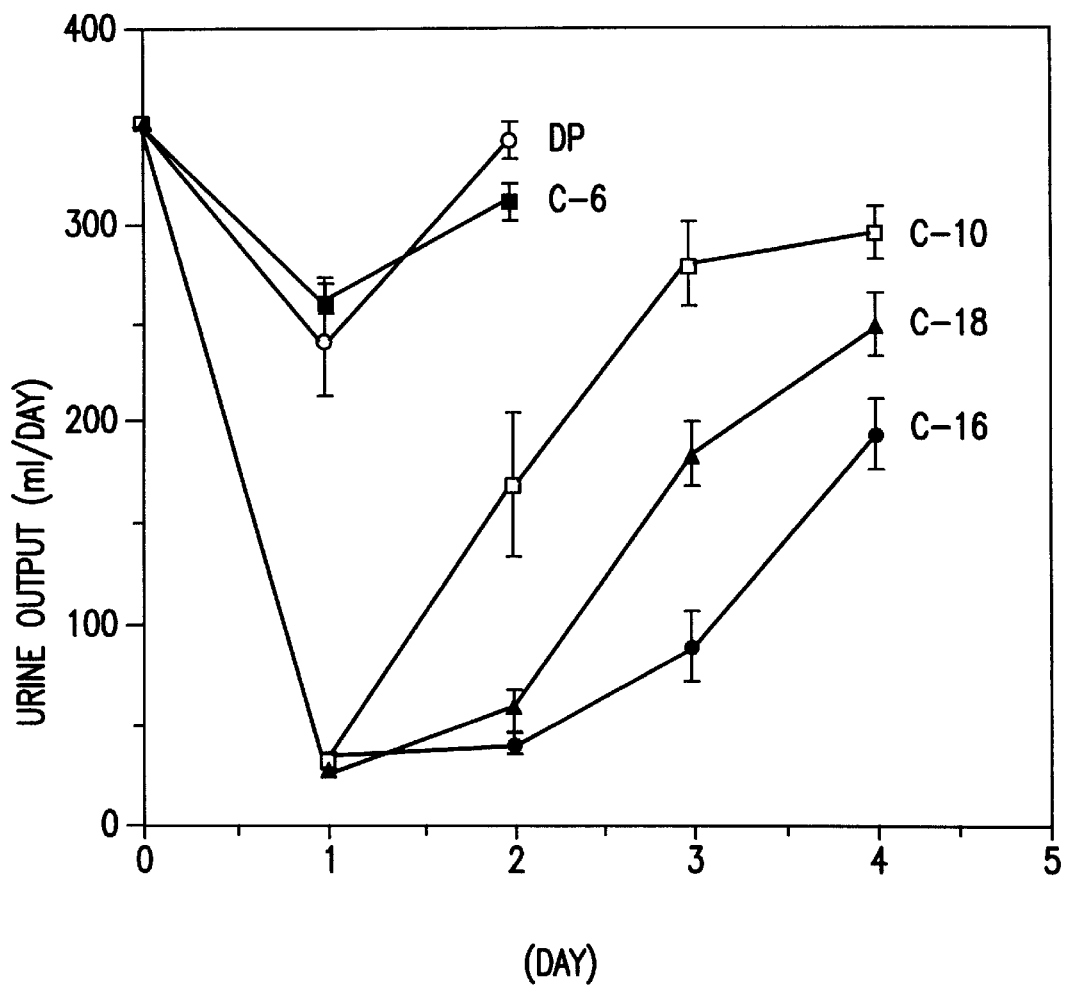
FIG. 9 is a graph which compares the structure-activity relationship of desmopressin-fatty acid conjugates in relation to the chain length of the fatty acid, at a dose of 0.5 μg/kg subcutaneous injection. "C-6" denotes caproic acid; "C-10" denotes capric acid; "C-16" denotes palmitic acid; and "C-18" denotes stearic acid.

In Vivo Structure-Activity Relationship of Desmopressin-Fatty Acid Conjugates DP, as well as its fatty acid derivatives, was tested for the anti-diuretic effects in Brattleboro rats. Three rats were injected s.c. with DP or its fatty acid conjugates at a dose of 0.5 μg/kg in 10% Liposyn® II (Abbott Laboratories). The urine output from each rat was measured, averaged, and plotted versus the number of days. As shown in FIG. 9, a minimum of 10 carbons is required for the fatty acid moiety in the DP-conjugates in order to increase the efficacy of the anti-diuretic activity.

Example 14

Figure 10:
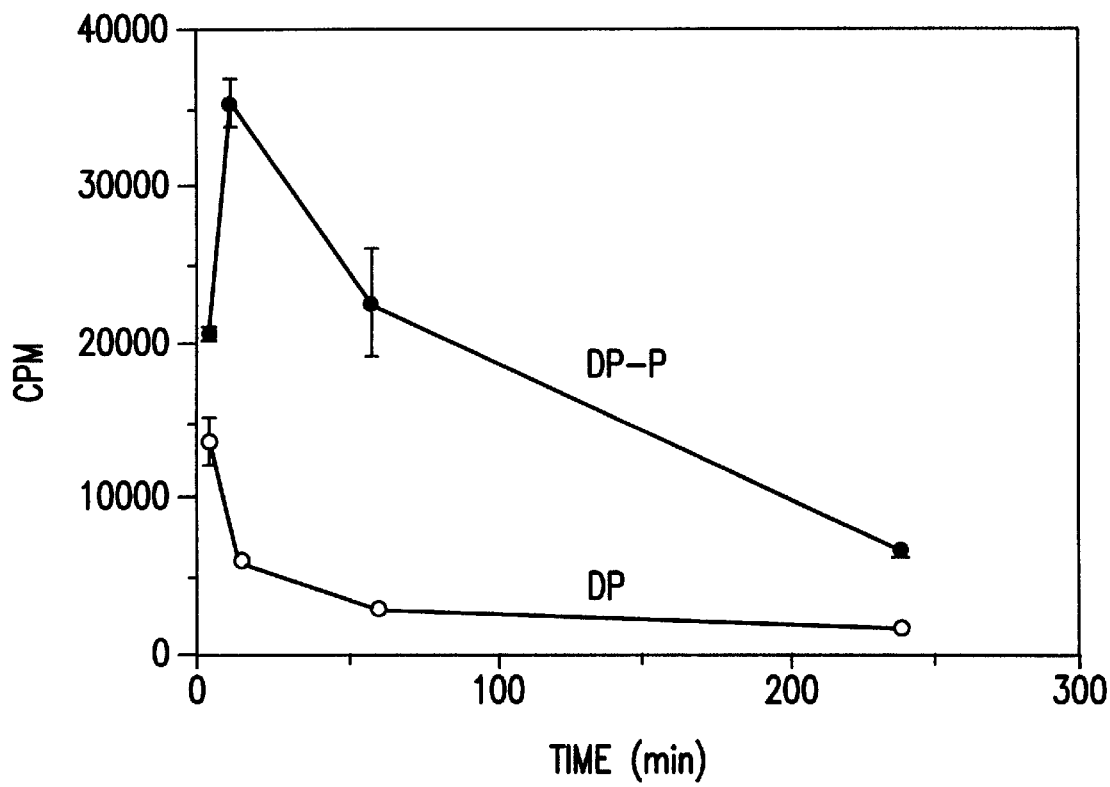
FIG. 10 is a graph which illustrates plasma desmopressin profiles following intravenous administration of desmopressin (DP) or its palmitic acid conjugate (DP-P) in mice.

In Vivo Distribution of Intravenously Administered Desmopressin-Palmitic Acid Conjugate (DP-P) in Mice Both DP and DP-P were iodinated with $^{125}$I by using the chloramine T method. $^{125}$I-DP or $^{125}$I-DP-P was injected intravenously to CF mice at a dose of $1 \times 10^6$ cpm/mouse. Groups of three treated mice were sacrificed at different time points and the radioactivity in the blood was measured by counting 0.2 ml of blood in a gamma counter. As shown in FIG. 10, the plasma half-life of DP-P is much longer than that of DP, resulting approximately a 6-fold increase in AUC.

Example 15

Synthesis of N-deoxycholyl 2-pyridyidithiocysteine (DOC-PDC)

A mixture of deoxycholic acid (585.2 mg), N-hydroxysuccinimide (230.0 mg), and dicyclohexylcarbodiimide (412.6 mg) in 25 ml of ethyl acetate was stirred at 25° C. for 16 hr. The dicyclohexylurea precipitate was removed by filtration and the ethyl acetate filtrate was evaporated under reduced pressure to obtain the product, N-hydroxysuccinimide ester of deoxycholic acid.

The crude N-hydroxysuccinimide ester of deoxycholic acid was re-dissolved in 10 ml of DMF, to which was added 533 mg of PDC, followed by 556.7 μl of triethylamine. The resultant suspension was stirred at 25° C. for 5 hr. This reaction mixture was then diluted with 80 ml of distilled water and acidified with HCl (6N) to pH 3. The DOC-PDC precipitate was isolated by centrifugation, re-suspended in 40 ml of distilled water, and the final solution was adjusted to pH 8 by using NaOH (5N). At this condition, DOC-PDC was dissolved in the aqueous solution and insoluble impurities were removed by centrifugation. The supernatant was re-acidified with HCl (6N) and DOC-PDC was collected by centrifugation and dried under the vacuum. The final product, as determined by TLC analysis, was practically pure and was used for the preparation of the conjugates without further purification.

Example 16

Synthesis of Desmopressin-Deoxycholic Acid (DP-DOC) Conjugates

DP-DOC was prepared by a similar procedure as described in Example 11. Briefly 280 μl of 10 mM DOC-PDC (10 mM, pH 7.7) was added to a solution of the reduced DP (0.5 ml of 1 mg/ml PBS). The mixture was stirred at 25° C. for 30 min when TLC analysis indicated that the conjugation reaction was completed. The reaction mixture was then acidified to pH 3 using HCl (1N) and the final product, DP-DOC, was isolated as the precipitate.

Example 17

Synthesis of Calcitonin-Palmitic Acid Conjugate (CT-P)

Salmon calcitonin (CT, 4 mg) was dissolved in 2 ml of PBS (pH 7.4) and treated with 46.6 μl of dithiothreitol (DTT, 0.1 M) at 37° C. for 30 min. The reduced calcitonin (dithiocalcitonin) was proceeded as such without isolation for the subsequent conjugation. To the reaction mixture was added 1.4 ml of 10 mM Pal-PDC (10 mM, pH 7.6). The mixture was stirred at 25° C. for 45 min and, subsequently, acidified to pH 3 using HCl (1N). The precipitate, which contained the palmityl disulfide conjugate of conjugate of calcitonin (CT-P) and the excess reagent, was dissolved in 1 ml of DMF. CT-P was purified by eluting in a Sephadex® LH20 column (40 ml) using DMF as the eluant. The fractions containing CT-P, which were eluted at the void volume of the column, were identified by TLC and UV (280 nm) analysis, and pooled. After evaporating the solvent under vacuum, a final product of 3.2 mg of CT-P was obtained.

Example 18

Figure 11A:
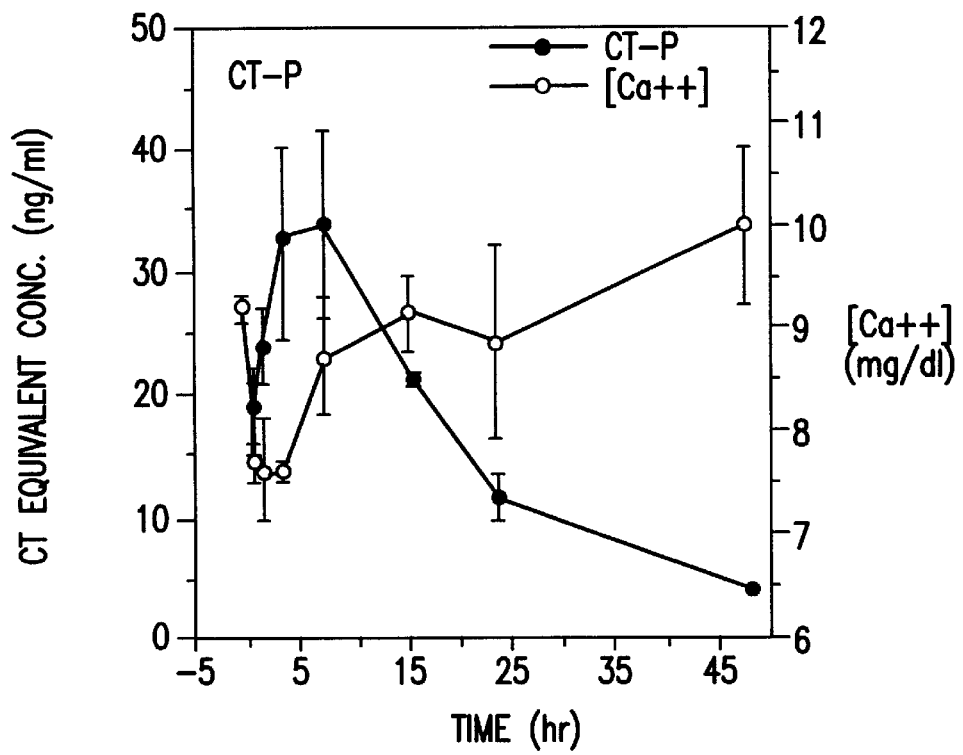
FIGS. 11A and 11B are graphs which illustrate the plasma calcitonin and calcium levels following subcutaneous administration of calcitonin (CT) or its palmitic acid conjugate (CT-P) in mice, at a dose of 100 μg/kg, (11A) illustrates the CT-P treatment; (11B) illustrates the CT treatment.
Figure 11B:
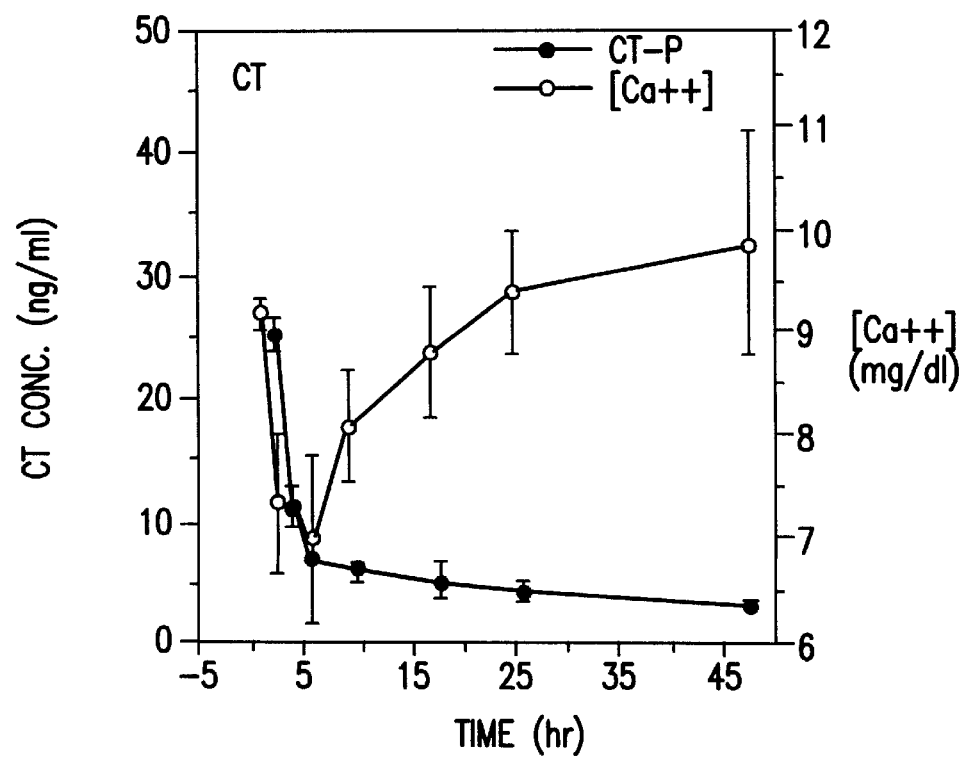

Sustained Release of Subcutaneously Administered Calcitonin (CP) and its Palmitic Acid Conjugate (CT-P) in Mice Both CT and CT-P were iodinated with $^{125}$I using chloramine T method. $^{125}$I-CT or $^{125}$I-CT-P was injected s.c. into mice at a dose of 125 μg/kg in 10% Liposyn® II (Abbott). Groups of three mice were sacrificed at different time points. The levels of calcium in the blood samples were determined by using a commercial calcium diagnostic kit (Sigma Chemical Co.). The plasma from each mouse was isolated and treated with 5% trichloroacetic acid (TCA) in an ice bath. The radioactivity in the hs TCA precipitates were considered as the intact CT in the plasma. As shown in FIG. 11, the plasma half-life of CT in CT-P-injected mice was significantly higher than that in CT-injected mice. CT-P-injected mice showed a transient reduction of the plasma calcium level, indicating that CT-P retains the in vivo biological activity of CP. More importantly, s.c. injected CT-P, in contrast to the rapid plasma clearance of s.c. injected CT, maintained an almost constant level of CT or CT-P in the blood for approximately 16 hours.

Example 19

Gastro-Intestinal Absorption and Calcium-Lowering Effect of Orally Administered Calcitonin-Palmitic Acid Conjugate (CT-P)

CT and CT-P were orally administered to CF mice using a gavaging needle at a dose of 100 μg/kg in PBS. The mice, three of each group, were sacrificed 1 hour after the treatment, and the plasma was isolated from their blood. The levels of CT and calcium were measured by using commercial CT-RIA (Phoenix) and calcium diagnostic (Sigma Chemical Co.) kits, respectively. The results are shown in Table 5. The level of RIA-detected CT in mice with oral administration of CT-P was significantly higher than that of CT. Furthermore, the level of calcium in plasma at 1 hour was lower in CT-P treated mice than that in CT treated mice, which was consistent with the finding in CT levels. Because the crossreactivity of CT-P to the anti-CT antibody is only about 10%, the actual concentration of total CT in the plasma of CT-P treated mice could be even higher than the value presented in Table 5.

TABLE 5

Plasma Calcitonin Concentrations and Calcium Reductions in Mice One Hour after the Oral Administration of CT and CT-P at a Dose of 100 µg/kg (N = 3, "S.D.)

|      | CT (pg/0.1 ml plasma) | Calcium (% reduction) |
|------|-----------------------|-----------------------|
| CT   | 9.2 ± 0.7             | 17.5 ± 3.6            |
| CT-P | 18.3 ± 4.0            | 28.9 ± 1.2            |

Example 20

Synthesis of Acyclovir-Lipoic Acid Ester Conjugate (ACV-LA)

The esterification between acyclovir (ACV) and lipoic acid (LA) was catalyzed by using dicyclohexylcarbodiimide in the presence of p-toluenesulfonic acid (TsOH). The product, ACV-LA was purified using preparative TLC.

Acyclovir (ACV, 25 mg), lipoic acid (LA, 229 mg), and dicyclohexylcarbodiimide (572.5 mg) were dissolved together in DMF (2.5 ml). To the resultant solution was added 10.8 mg of TsOH. The mixture was stirred at room temperature for 3 days. The dicyclohexylurea precipitate was removed by filtration. DMF in the filtrate was evaporated under vacuum. The residue from evaporation was suspended in 5 ml of deionized water and extracted with ethyl ether (2×3 ml). The aqueous layer was separated and lyophilized.

The lyophilized residue was redissolved in a small volume of methanol and loaded onto a preparative TLC plate. The plate was developed using methylene chloride:acetone:methanol (4:1:1) as the solvent system. An UV absorbance band of the product Rf=0.41), which was different from that of ACV (Rf=0.10), was identified and scraped from the TLC plate and the silica gel was extracted with 2×15 ml of the same solvent mixture as in the TLC. The solvent extract was evaporated in a rotary evaporator and a final product of 11.7 mg of ACV-LA was obtained.

Example 21

Synthesis of Acyclovir-Lipoic Acid-Dipalmitic Acid Conjugate (ACV-LA-DP)

The method for the preparation of the titled conjugate was similar to that of desmopressin-palmitic acid conjugate (Example 11). Acyclovir-lipoic acid ester (ACV-LA, 0.6 mg) was dissolved in 0.5 ml of PBS (pH 7.4) and treated with 14.5 ml of dithiothreitol (DTT, 0.1 M). The reduction was proceeded at 37° C. for 30 min. The reduced ACV-LA (dithiol compound) was used without further purification for the subsequent conjugation. To the reaction mixture was added 531 µl of 10 mM Pal-PDC (10 mM, pH 7.7). The mixture was stirred at 25° C. for 30 min. The reaction mixture was acidified to pH 3 using HCl (1N) and precipitation appeared. The precipitate, which contained ACV-LA-DP, was obtained. The product could be further purified by chromatographic methods.

Example 22

Effects of Liposomal Formulation on the Anti-Diuretic Action of Desmopressin-Palmitic Acid Conjugate (DP-P)

Liposomal DP-P, as well as DP-P in Tris® buffer, was tested for its ani-diuretic effects at an oral dose of 37.5 µg/kg in Brattleboro rats. To prepare liposomal DP-P, a metholic solution of dimyristoyl phosphatidyl choline, cholesterol and stearylamine (7:2:1) was evaporated to obtain a dry film. The film was hydrated in Tris® buffer (2 ml) containing appropriate amount of DP-P (2 hrs/25° C.), followed by probe sonication (15 min/37° C.). The resultant liposomal preparation was diluted with Tris® buffer to a total volume of 5 ml, which was used immediately. In rats treated with DP-P solution, the total volume of urine collected for the first five hours after oral administration was 53.3±15.3 ml, which was not significantly different from that of the control group (47.0±3.5 ml). However, liposomal DP-P showed a significant anti-diuretic effect with a total urine volume of 27.0±1.0 ml collected for the first five hours.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and any specific terms employed herein are intended in a descriptive sense and not for purposes of limitation. All publications, patents and patent applications cited herein are fully incorporated by reference herein.

What is claimed is:

1. A compound of formula (X):

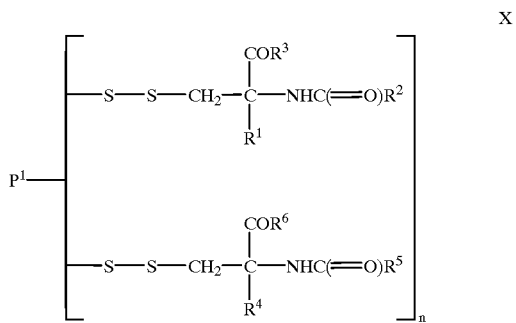

in which $P^1$ is a residue derived from a disulfide-containing compound or from the conjugation of two sulfhydryl-containing compounds which optionally may comprise a further disulfide group linked to a hydrophobic substituent of the formula:

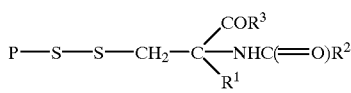

wherein each $R^1$ and $R^4$ are independently selected from the group consisting of hydrogen, lower alkyl or aryl; each $R^2$ and $R^5$ are independently a hydrophobic substituent; each $R^3$ and $R^6$ are independently selected from the group consisting of hydroxy, a hydrophobic substituent and an amino acid chain comprising one or two amino acids and terminating in —$CO_2H$ or —$COR^2$; n is an integer of from 1 to 20; wherein said hydrophobic substituent: (a) is selected from the group consisting of a lipid; an amino acid, dipeptide or polypeptide, any one of which is bonded to one or more lipids; and a steroid; or (b) taken together with the attached carbonyl is a fatty acid acyl group.

2. The compound of claim 1, wherein each $R^1$ is the same as $R^4$, each $R^2$ is the same as $R^5$, and each $R^3$ is the same as $R^6$.

3. The compound of claim 2, wherein each $R^1$ is hydrogen, each $R^2$ is part of a lipid group, each $R^3$ is hydroxy, and n is no greater than 10.

4. The compound of claim 2, wherein each $R^1$ is hydrogen, each $R^2$ is part of a fatty acid or steroid; and each $R^3$ is hydroxy.

5. The compound of claim 2, wherein said hydrophobic substitutent is part of a fatty acid residue having about 4 to about 26 carbon atoms.

6. The compound of claim 5, wherein said hydrophobic substitutent is part of a fatty acid residue having about 5 to about 19 carbon atoms.

7. The compound of claim 6, wherein said fatty acid is palmityl, oleyl or stearyl.

8. The compound of claim 2, wherein each $R^2$ is part of a steroid.

9. The compound of claim 8, wherein said steroid is selected from the group consisting of deoxycholate and cholate.

10. The compound of claim 1, wherein $P^1$ is selected from the group consisting of a peptide, a protein, an amino acid, a nucleotide, a nucleoside, a oligonucleotide, and a carbohydrate; or a derivative thereof.

11. The compound of claim 1, wherein said optional disulfide linked to a hydrophobic substituent is not present.

12. A pharmaceutical composition comprising the compound of claim 1 and a pharmaceutically acceptable carrier.

13. The pharmaceutical composition of claim 12, which is in the form of a liposome.

14. A method for increasing in vivo absorption in a mammal of a disulfide-group containing organic compound, said method comprising administering an effective amount the compound of claim 1 to the mammal.

15. The method of claim 14, wherein the disulfide group-containing organic compound is selected from the group consisting of a peptide, a protein, an amino acid, a nucleotide, a nucleoside, an oligonucleotide, and a carbohydrate; or derivative thereof.

16. The method of claim 14, wherein each $R^1$ and $R^4$ are hydrogen, each $R^2$ and $R^5$ are part of a lipid group, each $R^3$ and $R^6$ are hydroxy, and n is no greater than 10.

17. The method of claim 14, wherein each $R^1$ and $R^4$ are hydrogen, each $R^2$ and $R^5$ are part of a fatty acid or steroid; and each $R^3$ and $R^6$ are hydroxy.

18. A method for prolonging the in vivo blood and tissue retention, in a mammal, of a disulfide-group containing organic compound, said method comprising administering an effective amount of the compound of claim 1 to the mammal.

19. The compound of claim 18, wherein the disulfide group-containing organic compound is selected from the group consisting of a peptide, a protein, an amino acid, a nucleotide, a nucleoside, an oligonucleotide, and a carbohydrate; or a derivative thereof.

20. The method of claim 18, wherein each $R^1$ and $R^4$ are hydrogen, each $R^2$ and $R^5$ are part of a lipid group, each $R^3$ and $R^6$ are hydroxy, and n is no greater than 10.

21. The method of claim 18, wherein each $R^1$ and $R^4$ are hydrogen, each $R^2$ and $R^5$ are part of a fatty acid or steroid; and each $R^3$ and $R^6$ are hydroxy.

22. A method of making a compound of claim 1, said method comprising the steps of:
   a) reducing the disulfide-containing compound to form a reduced disulfide-containing compound; and
   b) reacting the reduced disulfide-containing compound with a compound of the general formula:

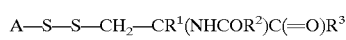

$$A—S—S—CH_2—CR^1(NHCOR^2)C(\!\!=\!\!O)R^3$$

in which A is an aromatic activating residue, whereby said compound is obtained.

23. The method of claim 22, wherein said disulfide-containing compound has more than one disulfide, and said disulfied-containing compound is partially reduced in step a).

24. The compound of claim 1, wherein n is 1.

25. A compound of formula (XI):

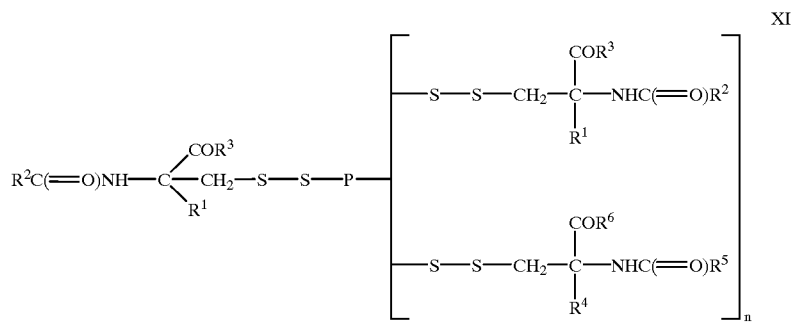

wherein P is a residue derived from a sulfhydryl-containing compound; each $R^1$ and $R^4$ are independently selected from the group consisting of hydrogen, lower alkyl or aryl; each $R^2$ and $R^5$ are independently a hydrophobic substituent; each $R^3$ and $R^6$ are independently selected from the group consisting of hydroxy, a hydrophobic substituent and an amino acid chain comprising one or two amino acids and terminating in —$CO_2H$ or —$COR^2$; n is an integer of from 1 to 20; wherein said hydrophobic substituent: (a) is selected from the group consisting of a lipid; an amino acid, dipeptide or polypeptide, any one of which is bonded to one or more lipids; and a steroid; or (b) taken together with the attached carbonyl is a fatty acid acyl group.

26. A method for making a compound of formula (XII):

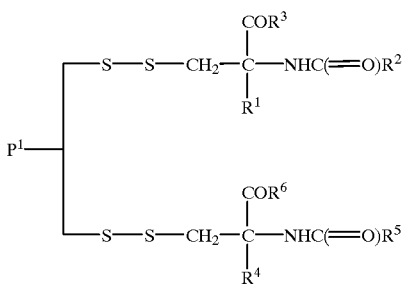

comprising conjugating a compound of general formula (VI$^1$):

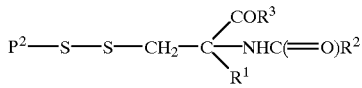

with a compound of general formula (VI$^2$):

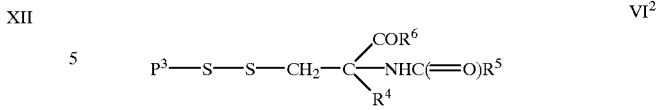

wherein,

R$^1$ and R$^4$ are different and each is selected from the group consisting of hydrogen, lower alkyl or aryl;

R$^2$ and R$^5$ are different and each is a hydrophobic substituent, wherein said hydrophobic substituent: (a) is selected from the group consisting of a lipid; an amino acid, dipeptide, or polypeptide, any one of which is bonded to one or more lipids; and a steroid; or (b) taken together with the attached carbonyl is a fatty acid acyl group;

R$^3$ and R$^6$ are different and each is selected from the group consisting of hydroxy, a hydrophobic substituent, and an amino acid chain comprising one or two amino acids and terminating in —CO$_2$H or —COR$^2$;

P$^1$ is the residue derived from the conjugation of P$^2$ and P$^3$; and

P$^2$ and P$^3$ are residues derived from sulfhydryl-containing compounds.

* * * * *

UNITED STATES PATENT AND TRADEMARK OFFICE
CERTIFICATE OF CORRECTION

PATENT NO. : 6,093,692

DATED : July 25, 2000

INVENTOR(S) : Shen et al.

It is certified that error appears in the above-identified patent and that said Letters Patent is hereby corrected as shown below:

In column 1, after the title and before the paragraph beginning at line 5, please insert the following:

*--Statement Regarding Federally Sponsored Research or Development*

This invention was made with government support under Contract No. UOI-CA 46496, awarded by the National Institutes of Health. The government has certain rights in the invention.--

In column 1, with regard to the "Inventors," please change the residence for Jinghua Wang from "South Pasadena" to --Arcadia--.

Signed and Sealed this

Twenty-fourth Day of April, 2001

Attest:

NICHOLAS P. GODICI

Attesting Officer

Acting Director of the United States Patent and Trademark Office